US008398789B2

(12) United States Patent
Wong et al.

(10) Patent No.: US 8,398,789 B2
(45) Date of Patent: Mar. 19, 2013

(54) FATIGUE-RESISTANT NICKEL-TITANIUM ALLOYS AND MEDICAL DEVICES USING SAME

(75) Inventors: Sophia L. Wong, Milpitas, CA (US); Zhicheng Lin, Palo Alto, CA (US); Alan G. Tahran, Jr., Manteca, CA (US)

(73) Assignee: Abbott Laboratories, Abbott Park, IL (US)

(*) Notice: Subject to any disclaimer, the term of this patent is extended or adjusted under 35 U.S.C. 154(b) by 583 days.

(21) Appl. No.: 12/324,732

(22) Filed: Nov. 26, 2008

(65) Prior Publication Data
US 2009/0165898 A1    Jul. 2, 2009

Related U.S. Application Data

(60) Provisional application No. 60/991,587, filed on Nov. 30, 2007, provisional application No. 60/991,965, filed on Dec. 3, 2007, provisional application No. 61/023,373, filed on Jan. 24, 2008, provisional application No. 61/048,119, filed on Apr. 25, 2008, provisional application No. 61/050,512, filed on May 5, 2008, provisional application No. 61/084,251, filed on Jul. 28, 2008.

(51) Int. Cl.
*A61L 27/06* (2006.01)
*C22C 14/00* (2006.01)

(52) U.S. Cl. ..... 148/563; 148/564; 623/1.18; 623/23.53

(58) Field of Classification Search .......... None
See application file for complete search history.

(56) References Cited

U.S. PATENT DOCUMENTS

| | | | | |
|---|---|---|---|---|
| 5,419,788 A | * | 5/1995 | Thoma et al. | 148/402 |
| 6,342,067 B1 | * | 1/2002 | Mathis et al. | 623/1.15 |
| 2003/0199236 A1 | * | 10/2003 | Aloise et al. | 451/48 |
| 2004/0216814 A1 | * | 11/2004 | Dooley et al. | 148/563 |
| 2006/0014480 A1 | * | 1/2006 | Aloise et al. | 451/149 |
| 2007/0073374 A1 | * | 3/2007 | Anderl et al. | 623/1.2 |
| 2007/0289677 A1 | * | 12/2007 | Ma et al. | 148/563 |

FOREIGN PATENT DOCUMENTS

| | | |
|---|---|---|
| WO | WO 2005/049876 | 6/2005 |
| WO | WO 2007/147156 | 12/2007 |
| WO | WO 2008/030517 | 3/2008 |
| WO | WO 2009/070784 | 6/2009 |

OTHER PUBLICATIONS

Tobushi, H. et al. "Recovery Stress Due to R-Phase Transformation in Ni-Ti Shape Memory Alloy", Proceedings of the First International Conference on Shape Memory and Superelastic Technologies, SMST International Committee, 1994.*
U.S. Appl. No. 60/991,587, filed Nov. 30, 2007, Lin et al.
U.S. Appl. No. 60/991,965, filed Dec. 3, 2007, Lin et al.
U.S. Appl. No. 61/023,373, filed Jan. 24, 2008, Lin et al.
U.S. Appl. No. 61/048,119, filed Apr. 25, 2008, Wong et al.
U.S. Appl. No. 61/050,512, filed May 5, 2008, Wong et al.
U.S. Appl. No. 61/084,251, filed Jul. 28, 2008, Wong et al.

(Continued)

*Primary Examiner* — George Wyszomierski
(74) *Attorney, Agent, or Firm* — Workman Nydegger; Ron Devore

(57) ABSTRACT

Superelastic and/or shape memory nickel-titanium alloys having an increased fatigue life that is superior to known nickel-titanium alloys are disclosed. The nickel-titanium alloys have a minimum fatigue life that may be at least about 10 million strain cycles at a strain of at least about 0.75. The minimum fatigue life may be due, at least in part, to the nickel-titanium alloy having at least one of an oxygen concentration of less than about 200 ppm, a carbon concentration of less than about 200 ppm, the absence of oxide-based and/or carbide-based inclusions having a size greater than about 5 microns (µm), the presence of an R-phase, or combinations of the foregoing. Articles manufactured from such fatigue-resistant nickel-titanium alloys can be more durable because they are more resistant to repetitive strain and crack propagation.

22 Claims, 11 Drawing Sheets

OTHER PUBLICATIONS

S.W. Robertson et al. "Cyclic Fatigue of Nitinol", Oct. 3, 2004, XP55028804.

Patel el al. "An Investigation of Divers Surface Finishes on Fatigue Properties of Superelastic Nitinol Wire," May 1, 2006, XP55028821.

* cited by examiner

FATIGUE-RESISTANT NICKEL-TITANIUM ALLOYS AND MEDICAL DEVICES USING SAME

CROSS-REFERENCE TO RELATED APPLICATIONS

This application claims priority to U.S. Provisional Patent Application Nos. 60/991,587 and 60/991,965, entitled "METHODS FOR PRODUCING FATIGUE RESISTANT MEDICAL DEVICES USING NITINOL AND ALLOYS THEREOF," and filed Nov. 30, 2007 and Dec. 3, 2007, respectively, and U.S. Provisional Patent Application No. 61/023,373, entitled "METHODS FOR PRODUCING FATIGUE RESISTANT MEDICAL DEVICES USING NITINOL AND ALLOYS THEREOF," and filed Jan. 24, 2008, and U.S. Provisional Patent Application Nos. 61/048,119 and 61/050,512 entitled "METHODS FOR PRODUCING FATIGUE RESISTANT MEDICAL DEVICES" filed Apr. 25, 2008 and May 5, 2008, respectively, U.S. Provisional Patent Application No. 61/084,251 entitled "METHODS FOR PRODUCING FATIGUE RESISTANT MEDICAL DEVICES" filed Jul. 28, 2008, each of which are hereby incorporated by reference.

FIELD OF THE INVENTION

The present disclosure relates generally to medical devices, and more particular to fatigue resistant medical devices incorporating nickel-titanium alloys and methods for producing the same.

BACKGROUND OF THE INVENTION

Medical devices may be subject to multiple stresses and strains, such as after insertion into a body lumen. Due to the constant stresses and strains placed upon a medical device, microcracks may eventually form on a surface of or within a medical device leading to structural failure and/or patient injury. Increasing the overall strength of a medical device can lead to overrigidity and/or inflexibility, which can unintentionally injure a patient and/or cause further medical complications.

One type of material commonly used for medical devices to attempt to alleviate some of these difficulties is a shape memory alloy. A shape memory alloy has superelastic material characteristics above a transformation temperature and shape memory characteristics below a transformation temperature. Superelastic materials possess unique characteristics that are particularly useful in medical applications. If a piece of a shape memory alloy, such as nitinol, is mechanically stretched, compressed, bent, or twisted in its martensitic phase, it will return to its original configuration upon heating.

The malleable martensitic form of the alloy can be easily deformed and if not constrained, will freely recover upon heating to its original, much stronger austenite phase. In theory, this cycle can be repeated indefinitely. However, microcracks may begin to form through environmental stresses to which the shape memory alloy is subjected. These microcracks can eventually lead to a traumatic structural failure within the shape memory alloy.

Various medical devices incorporating the use of shape memory elements have been known for a number of years. Medical devices adopting the use of shape memory elements rely on the unique structural properties of shape memory alloys in order to achieve their desired effects. The shape memory alloys that are used in stents, for example, retain their new shape when cooled to the martensitic state and are thereafter deformed. However, these same shape memory alloys will recover their original shape when warmed to the austenitic state.

BRIEF SUMMARY OF THE INVENTION

The present disclosure generally relates to superelastic and/or shape memory nickel-titanium alloys having an increased fatigue life that is superior to known nickel-titanium alloys. Increased fatigue life lengthens the useful lifespan of articles manufactured from superelastic and/or shape memory nickel-titanium alloys due to, for example, reduced incidence of crack propagation as a result of repetitive strain. Increased fatigue life also improves patient safety by reducing failure rates of implantable articles made from superelastic and/or shape memory nickel-titanium alloys. The endoprosthetic devices disclosed herein may be adapted for implantation in a body lumen, such as an artery or a vein. It is recognized, however, that the present superelastic and/or shape memory nickel-titanium alloys and methods for their manufacture are not limited to endoprostheses and may be used in various other devices (e.g., closure elements and guidewires) and components thereof.

In one embodiment, a fatigue-resistant superelastic or shape-memory nickel-titanium alloy is disclosed. The fatigue-resistant superelastic or shape-memory nickel-titanium alloy can be used, for example, to form at least a portion of an implantable endoprosthetic device. The fatigue-resistant superelastic or shape-memory alloy includes nickel-titanium and nickel-titanium-platinum alloys having a minimum fatigue life that is superior to known nickel-titanium alloys.

The minimum fatigue life of the fatigue-resistant superelastic or shape-memory nickel-titanium alloys disclosed herein may be at least about 10 million strain cycles at a strain greater than about 0.75%, 0.76%, 0.77%, 0.78%, 0.79%, 0.80%, 0.85%, 0.9%, or 0.95%, as measured using, for example, a rotating beam fatigue testing apparatus (other techniques for measuring the strain can also be used). In one embodiment, the member formed from the fatigue-resistant superelastic or shape-memory nickel-titanium alloy is able to survive at least about 10 million strain cycles at a strain in a range from about 0.76% to about 1.25%, more preferably at least about 10 million strain cycles at a strain in a range from about 0.78% to about 1.2%, alternatively 0.8% to about 1.15% or at least about 10 million strain cycles at a strain in a range from about 0.85% to about 1.05%.

The minimum fatigue life may be due, at least in part, to the nickel-titanium alloy having at least one of an oxygen concentration of less than 200 ppm, a carbon concentration of less than about 200 ppm, or a presence of an R-phase therein.

It is believed that limiting the oxygen content and/or the carbon content in the nickel-titanium alloy may increase the fatigue life nickel-titanium alloy by reducing level the numbers of oxide-based and/or carbon-based inclusions. Oxide-based and/or carbon-based inclusions contribute to failure of articles made from nickel-titanium alloys by contributing to the formation of stress-induced cracks, for example. Reducing the numbers of oxide-based and/or carbon-based inclusions contributes to increased fatigue life by making it less likely that stress-induced cracks will form.

The R-phase in the nickel-titanium alloy is a stable transition phase between the austenite phase and the martensite phase. Nickel-titanium alloys having the R-phase may have an increased fatigue life because the alloy experiences less internal stress for a given amount of strain. The R-phase in the nickel-titanium alloy may be formed, for example, by treating the alloy (e.g., cold working, hot working, grinding, and/or pre-fatiguing) so a stress-induced transformation from the austenitic phase to the R-phase occurs.

In one embodiment, an implantable device formed from a fatigue-resistant superelastic or shape-memory nickel-titanium alloy is disclosed. The implantable device includes at least one structural member sized and configured for implantation into a living subject. The at least one structural member may be formed from a nickel-titanium alloy having a minimum fatigue life of at least about 10 million strain cycles at a strain greater than about 0.75%.

In one aspect, the minimum fatigue life of the at least one structural member may be due, at least in part, to the at least one structural member having a ground surface and at least one thickness dimension of about 0.03 mm to about 0.35 mm, being fabricated from a nickel-titanium alloy having an R-phase therein, being fabricated from a nickel-titanium alloy having an oxygen concentration of less than about 200 ppm, being fabricated from a nickel-titanium alloy having a carbon concentration of less than about 200 ppm, or combinations thereof.

In one embodiment, an implantable endoprosthetic device including at least one structural member formed from a fatigue-resistant superelastic or shape-memory nickel-titanium alloy manufactured according to a method that includes (1) providing a fatigue-resistant superelastic or shape-memory nickel-titanium alloy having a first state, (2) forming the alloy into a first member having a minimum fatigue life defined by survival of at least about 10 million strain cycles at a strain greater than about 0.75%, and (3) assembling an implantable device that includes at least the first member.

In one embodiment, providing a fatigue-resistant superelastic or shape-memory nickel-titanium alloy having a first state can include at least one sourcing starting materials having a desirable measure of purity, including selecting raw titanium sponge having an oxygen content less than 200 ppm, preparing the fatigue-resistant superelastic or shape-memory nickel-titanium alloy in a substantially oxygen free environment, preparing the fatigue-resistant superelastic or shape-memory nickel-titanium alloy in a substantially carbon-free environment, forming an ingot of the fatigue-resistant superelastic or shape-memory nickel-titanium alloy in an environmental volume of the having a reduced size, removing a portion of an ingot of the fatigue-resistant superelastic or shape-memory nickel-titanium alloy to remove impurities from the fatigue-resistant superelastic or shape-memory nickel-titanium alloy, determining the oxygen content of at least a portion of the fatigue-resistant superelastic or shape-memory nickel-titanium alloy, and rejecting alloys having an oxygen content greater than 200 ppm, determining the carbon content of at least a portion of the fatigue-resistant superelastic or shape-memory nickel-titanium alloy, and rejecting alloys having a carbon content greater than about 200 ppm, or determining the presence and/or size of inclusions, voids, surface defects, and/or other defects using at least one of scanning electron microscopy, energy dispersive x-ray spectroscopy, eddy currents, inert gas diffusion, and/or other content determination processes, and rejecting alloys having oxide and/or carbide inclusions greater than about 5 microns (μm) in size. Surprisingly and unexpectedly, it was found that the presence of oxide and/or carbide inclusions having a size greater than about 5 microns in size was detrimental at substantially any concentration.

In one embodiment, preparing the fatigue-resistant superelastic or shape-memory nickel-titanium alloy in a substantially oxygen free environment includes at least one of: melting the alloy in a furnace using shielding gases that exclude oxygen, melting the alloy in a vacuum furnace, or scavenging oxygen and oxide forming species from a melting furnace using a strong oxide former prior to melting the fatigue-resistant superelastic or shape-memory nickel-titanium alloy in the furnace.

In one embodiment, preparing the fatigue-resistant superelastic or shape-memory nickel-titanium alloy in a substantially carbon-free environment includes replacing carbon tooling with non-carbon tooling.

In one embodiment, removing a portion of the ingot of the fatigue-resistant superelastic or shape-memory nickel-titanium alloy can include removing portions of the ingot that are most likely to contain impurities that form oxide-based and/or carbide-based impurities. For example, light and heavy impurities can be removed from the ingot by removing an upper portion of the ingot (e.g., about 10%) and a lower portion of the ingot (e.g., about 10%). In another embodiment, the portion of the ingot that typically has the highest oxygen content can be found generally at the center. As such, removing a generally central portion of the ingot (e.g., about 25% of the center portion) removes the portion that is most likely to include oxide-based inclusions. In yet another embodiment, removing an outer portion of the ingot (about 5% between the upper portion and the lower portion) typically removes impurities that can come from the furnace and/or cast.

In one embodiment, the alloy that is provided is formed into a first structural member having a first state. In one embodiment, the first state can be an unfinished state and/or an intermediate state of the alloy and/or the structural member. As such, the first state may be transformed into a second state in the process of finishing the alloy and/or the structural member into a completed endoprosthetic device.

In one embodiment, the forming can include at least one of drawing, work hardening, annealing, laser cutting, thermal cutting, EDM, milling, chemical etching, hydro-cutting, water jetting, vapor deposition, electroplating, spraying, welding, bonding, sintering, or energy streaming, and combinations thereof.

In one embodiment, the structural member in the first state is transformed into a structural member having a second state via one or more treatment processes. In one aspect of the present disclosure, it is generally believed that the so-called second state is primarily responsible for imparting the increased fatigue life of the nickel-titanium alloys disclosed herein.

In one embodiment, the first member may be treated to form the R-phase in at least a portion of the nickel-titanium alloy. The treating process may include at least one of: grinding the first member so as to reduce at least one thickness dimension thereof to form an R-phase in at least a portion of the nickel-titanium alloy and thereby lower the Young's modulus of the selected and manufactured alloy, or pre-fatiguing the first member to form an R-phase in at least a portion of the nickel-titanium alloy and thereby lower the Young's modulus of the selected and manufactured alloy.

In one embodiment, assembling an implantable device that includes at least the first member in the second state can include at least one of connecting at least two portions of the first member, shaping the first member, cutting the first member, and/or applying surface finish to the first member.

In one embodiment, a surface finish is applied to the first member. It has been found that having a defect-free surface finish that is free of surface flaws such as microcracks and/or inclusions can help to impart an increased fatigue life. In one embodiment, applying a surface finish to the first member can include mechanically finishing the first member using bead blasting, tumbling, grinding, laser energy finishing, and/or other mechanical finishing. In another embodiment, applying a surface finish to the first member can include electropolishing the first member. In some embodiment, applying the surface finish can include both mechanical and chemical finishing (i.e., electropolishing) steps.

In one embodiment, endoprostheses of the present disclosure are configured for use in a body of a living subject. As such, the present disclosure includes a method of delivering an endoprosthesis into a body of a subject. Such a method includes: (1) providing an endoprosthesis as described herein, (2) orienting the endoprosthesis into a delivery orientation, (3) inserting the endoprosthesis in the delivery orientation into a delivery device, (4) delivering the endoprosthesis to a desired deployment site within the body lumen of the subject, (5) removing the endoprosthesis from the delivery device, and (6) implanting the implantable endoprosthetic device at the delivery site.

In one embodiment, the implantable endoprosthetic device is a stent. Examples of stent include self-expanding stents and/or balloon expandable stents that can be used to scaffold an artery or vein. In another embodiment, the implantable endoprosthetic device is a closure element. In yet another embodiment, the implantable endoprosthetic device is a guide wire.

In one embodiment, the present disclosure includes a method for using an implantable endoprosthetic device. Such a method includes: (1) providing an endoprosthesis as described herein, and (2) implanting the implantable endoprosthetic device at a delivery site in the living subject.

These and other objects and features of the present disclosure will become more fully apparent from the following description and appended claims, or may be learned by the practice of the disclosure as set forth hereinafter.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof, which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings.

Figure 1:
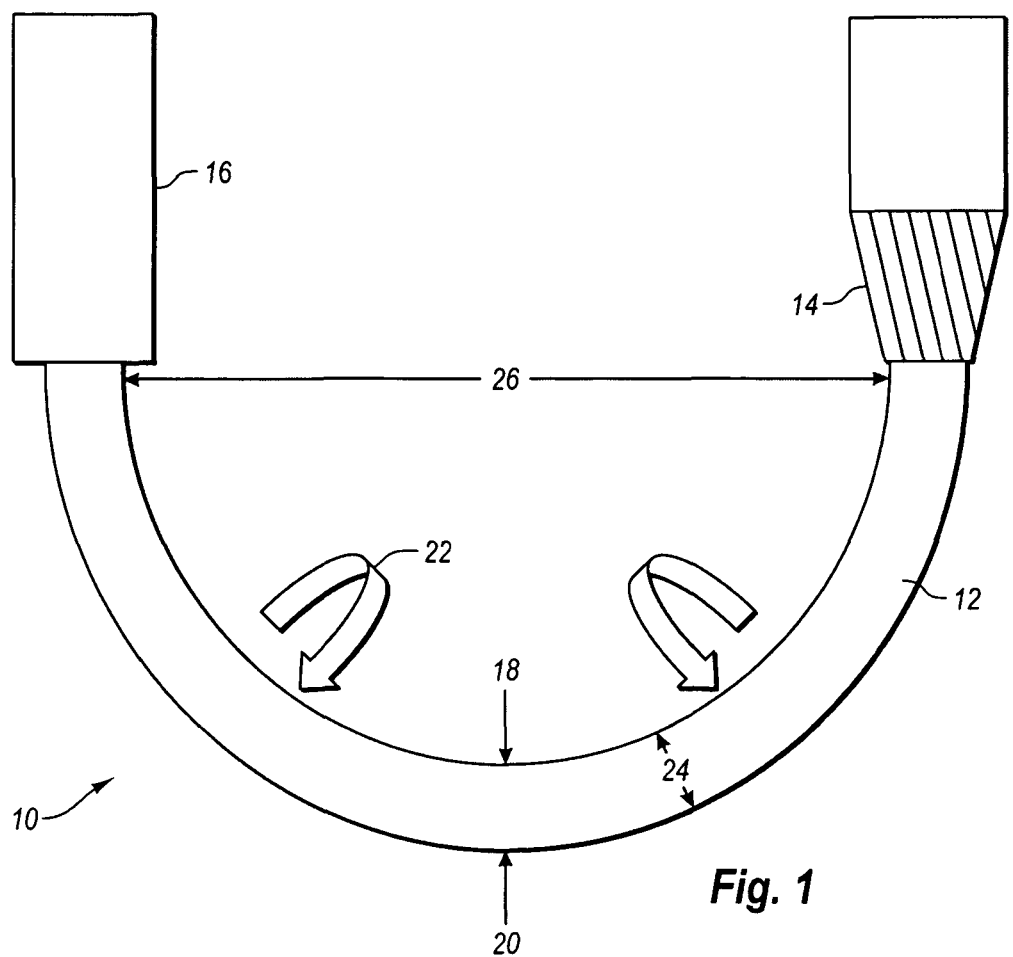
FIG. 1 illustrates a rotating beam fatigue testing apparatus.

It should be noted that the figures are not drawn to scale and that elements of similar structures or functions are generally represented by like reference numerals for illustrative purposes throughout the figures. It also should be noted that the figures are only intended to facilitate the description of embodiments of the present disclosure.

DETAILED DESCRIPTION

I. Introduction

Fatigue-resistant superelastic and/or shape-memory nickel-titanium alloys and medical devices fabricated from said nickel-titanium alloys are described. Medical devices may include implantable devices, such as stents, closure elements, and/or other implantable devices, and/or other medical devices. Embodiments of fatigue-resistant medical devices may include a material made from any of the disclosed nickel-titanium alloys and articles made therefrom discussed herein. Under certain conditions, such nickel-titanium alloys have a shape memory effect in which a particular shape can be set. For example, once a shape is set, the nickel-titanium alloy may be bent out of shape or deformed and then returned to its original shape upon heating to a set temperature or upon removal of a restraint. Above the austenite finish temperature, nickel-titanium alloys can exhibit a transformation-induced recoverable strain and are often referred to as being superelastic.

A nickel-titanium alloy can have any non-characteristic initial shape that can then be configured into a memory shape by heating the nickel-titanium alloy and conforming it into the desired memory shape. After the nickel-titanium alloy is cooled, the desired memory shape can be retained. This allows for the nickel-titanium alloy to be bent, compacted, and placed into various contortions by the application of requisite forces; however, after the forces are released, the nickel-titanium alloy can be capable of returning to the memory shape.

Fatigue-resistant superelastic and/or shape-memory nickel-titanium alloys according to the present disclosure may generally include about 50 atomic % nickel (at % N), and about 50 atomic % titanium (at % Ti), wherein the percentage of nickel can increase by about 2% to about 3% while maintaining superelasticity. More particularly, fatigue-resistant superelastic and/or shape-memory nickel-titanium alloys according to the present disclosure may generally include about 50.8 at % N and about at % Ti. Radiopaque nickel-titanium alloys, which are a type of a nickel-titanium alloy, may have a composition of nickel, titanium, and one or more additional alloying elements. The addition of one or more additional elements may preserve the superelastic and/or shape-memory qualities of such nickel-titanium alloys, while improving the material's radiopacity and/or fatigue life.

The atomic percentage of nickel in a radiopaque nickel-titanium alloy, in some compositions, may range from about 38 at % N to about 40 at % N. The atomic percentage of titanium in radiopaque nickel-titanium alloys, in some compositions, may range from about 44.5 at % Ti to about 54.5 at % Ti. The one or more alloying elements may be selected from the group consisting of iridium, platinum, gold, rhenium, tungsten, palladium, rhodium, tantalum, silver, ruthenium, and hafnium.

In one embodiment, radiopaque nickel-titanium may generally include about 43 at % N, about 49.5 at % Ti, and about 7.5 at % Pt. In another embodiment, a radiopaque nickel-titanium alloys may generally include from about 38 at % Ni to about 48 at % Ni, from about 44.5 at % Ti to about 54.5 at % Ti, and from about 2.5 at % Pt to about 12.5 at % Pt. In a further embodiment, the atomic percentage of platinum is greater than or equal to about 2.5% and less than or equal to about 15%. In an alternative embodiment, the atomic percentage of palladium is greater than or equal to about 2.5% and less than or equal to about 20%. In one embodiment, a radiopaque nickel-titanium alloy may have a composition including from about 30 at % Ti to about 52 at % Ti and the balance nickel and up to 10 at % of one or more additional alloying elements.

In various alternative embodiments, a minor addition of a quaternary element is contemplated; for example, iron, to further enhance the alloy's formability or its thermomechanical properties. The presence of impurities such as carbon or oxygen or the like in the nickel-titanium alloys is also possible.

In the present case, fatigue-resistant superelastic and/or shape-memory nickel-titanium alloys can be trained to remember a certain shape, straightened in a shaft, catheter, or other tube, and then released from the catheter or tube to return to its trained shape. The nickel-titanium alloy may be utilized having linear elastic properties or non-linear elastic properties.

An endoprosthesis body having at least one layer made of a nickel-titanium alloy and other suitable layers can be compressed or restrained in its delivery configuration within a delivery device using a sheath or similar restraint, and then deployed to its desired configuration at a deployment site by removal of the restraint as is known in the art. An endoprosthesis body made of a thermally-sensitive material can be deployed by exposure of the endoprosthesis to a sufficient temperature to facilitate expansion.

Embodiments of fatigue resistant implantable devices may be formed according to the methods and materials described in U.S. Provisional Patent Application Nos. 60/991,587 and 60/991,965, entitled "METHODS FOR PRODUCING FATIGUE RESISTANT MEDICAL DEVICES USING NITINOL AND ALLOYS THEREOF," and filed Nov. 30, 2007 and Dec. 3, 2007, respectively, and U.S. Provisional Patent Application No. 61/023,373, entitled "METHODS FOR PRODUCING FATIGUE RESISTANT MEDICAL DEVICES USING NITINOL AND ALLOYS THEREOF," and filed Jan. 24, 2008, and U.S. Provisional Patent Application Nos. 61/048,119 and 61/050,512 entitled "METHODS FOR PRODUCING FATIGUE RESISTANT MEDICAL DEVICES" filed Apr. 25, 2008 and May 5, 2008, respectively, U.S. Provisional Patent Application No. 61/084,251 entitled "METHODS FOR PRODUCING FATIGUE RESISTANT MEDICAL DEVICES" filed Jul. 28, 2008, each of which are hereby incorporated by reference.

II. Fatigue-Resistant Nickel-Titanium Alloys and Implantable Endoprostheses

The present disclosure generally relates to superelastic and/or shape memory nickel-titanium alloys having an increased fatigue life that is superior to known nickel-titanium alloys. Increased fatigue life lengthens the useful lifespan of articles manufactured from superelastic and/or shape memory nickel-titanium alloys due to, for example, reduced incidence of crack propagation as a result of repetitive strain. Increased fatigue life also improves patient safety by reducing failure rates of implantable articles made from superelastic and/or shape memory alloys. The endoprosthetic devices disclosed herein may be adapted for implantation in a body lumen, such as an artery or a vein. It is recognized, however, that the present superelastic and/or shape memory nickel-titanium alloys and methods for their manufacture are not limited to endoprostheses and may be used in various other devices (e.g., closure elements and guidewires) and components thereof.

In one embodiment, a fatigue-resistant superelastic or shape-memory nickel-titanium alloy is disclosed. The fatigue-resistant superelastic or shape-memory nickel-titanium alloy can be used, for example, to form at least a portion of an implantable endoprosthetic device. The fatigue-resistant superelastic or shape-memory nickel-titanium alloy may be a binary nickel-titanium alloy, or a ternary or greater nickel-titanium alloy (e.g., Ni—Ti—Pt alloy) having a minimum fatigue life that is superior to known nickel-titanium alloys.

The minimum fatigue life of the nickel-titanium alloys, according to the present disclosure, may be defined by survival of structural member formed from a nickel-titanium alloy of at least about 10 million strain cycles at a strain greater than about 0.75%, 0.76%, 0.77%, 0.78%, 0.79%, 0.80%, 0.85%, 0.9%, or 0.95%. In one embodiment, the minimum fatigue life may be defined by survival of structural member formed from a nickel-titanium alloy of at least about 10 million strain cycles at a strain in a range from about 0.76% to about 1.25%, more preferably at least about 10 million strain cycles at a strain in a range from about 0.78% to about 1.2%, alternatively 0.8% to about 1.15% or at least about 10 million strain cycles at a strain in a range from about 0.85% to about 1.05%.

The minimum fatigue life defined herein can be tested using any suitable means of fatigue testing known in the art. For example, a suitable means of fatigue testing includes use of a rotating beam test method. A typical rotating beam testing apparatus 10 is depicted in FIG. 1. In the rotating beam fatigue test, a specific length of wire 12 having a defined diameter 24 is bent in a defined radius 26 and forced to rotate 22. The portion of the wire at the apex of the curve experiences an alternating stain, which is defined by Equation 1:

$$e = (r/r+R) \cdot 100 \qquad \text{Equation 1}$$

where 'r' is the diameter of the test sample (i.e., the wire diameter) and R is the width of the bend to which the test sample is subjected.

As can be seen in FIG. 1, a length of wire 12 is bent between two fixed points 14 and 16. One end of the wire 12 is held by a chuck 14 that rotates the wire 12, while the other end of the wire is held by a bushing 16 that allows the wire to freely rotate 22 when chuck 14 is rotated. The middle section of the wire at the apex of the curve experiences the highest deformation between compression 18 and tension 20 due to the rotation. It should be noted, however, that the present disclosure is not limited to a structural member that is a round wire. While a rotating beam fatigue test is particularly suited to testing samples having a round cross-section, the fatigue lives disclosed herein relative to NiTi and NiTi alloys and methods for preparing such alloys are applicable to a structural member having any cross-section. Moreover, fatigue lives determined using means other testing means should be comparable to fatigue lives determined using a rotating beam fatigue testing apparatus.

The applicants have found that the minimum fatigue life can be increased by a number of processes. For example, an increase in the minimum fatigue life that will, in turn, increase the useful lifespan of articles manufactured form the alloys discussed herein can be imparted by controlling the oxygen content of the alloys. In one embodiment, the fatigue life of a nickel-titanium alloy can be increased if the oxygen content is less than about 200 ppm, or preferably less than about 100 ppm, or more preferably less than about 50 ppm.

Conventional nickel-titanium alloys typically have a large amount of dissolved oxygen because titanium has a high affinity for oxygen. For example, it is typical for titanium and/or titanium alloys to scavenge large amounts of oxygen while the material is molten such as during a manufacturing process. However, if the level of dissolved oxygen exceeds solubility limits, oxide-containing inclusions will tend to form as the material cools. These oxide-containing inclusions are problematic because they contribute to stress failure modes, such as cracking and fracturing that can lead to failure of articles manufactured from superelastic and/or shape-memory alloys.

The minimum fatigue life of articles manufactured from nickel-titanium alloys can also be increased by reducing the amount of carbon contamination therein. Because the temperatures used to melt nickel-titanium alloys and elemental constituents thereof are typically very high, carbon-based tools are typically used during the melting process. For example, graphite crucibles are typically used for handling molten nickel-titanium alloys and elemental constituents thereof such as titanium and nickel. However, the carbon in the carbon-based tooling may be absorbed by the nickel-titanium alloy and/or its elemental constituents during the melting process. When carbon exceeds the solid solubility limit for a nickel-titanium alloy, carbon-containing inclusions will tend to form upon cooling. As with the oxide-containing inclusion discussed above, carbon-based inclusions can contribute to fatigue failure of articles manufactured from superelastic and/or shape-memory nickel-titanium alloys.

The amount of carbon introduced into nickel-titanium alloys may be reduced by using non-carbon-based tooling. Examples of non-carbon-based tooling may include water-cooled copper, ceramic, glass, and/or other tooling that does not provide carbon in a sufficient amount so that carbon-based inclusions form in the nickel-titanium alloys.

It is also believed that there is some degree of interdependence between the solid solubility limits for oxygen and carbon. That is, presence of one reduces the solubility of the other. As such, it is desirable to limit both the oxygen content and carbon contamination in the nickel-titanium alloys discussed herein.

The general formulae for carbon-based and oxide-based inclusions in nickel-titanium alloys are TiC (titanium carbide), $Ti_4Ni_2O_y$, and/or $Ti_4(NiX)_2O_y$. In the present context, X can be any one of Ir, Pt, Au, Re, W, Pd, Rh, Ta, Ag, Ru, or Hf, and combinations thereof, although other elemental combinations are possible.

The minimum fatigue life of articles manufactured from nickel-titanium alloys can also be increased by the presence of the so-called "R-phase" in a superelastic and or shape-memory nickel-titanium alloy. The R-phase of a superelastic nickel-titanium alloy is a transformation phase between an austenitic phase and a martensitic phase that occurs when stress or another force is applied at a temperature below either the austenitic start temperature or the martensitic start temperature.

Superelastic and/or shape memory nickel-titanium alloys having the R-phase can have a significantly longer fatigue life than nickel-titanium alloys that are in the form of the austenitic phase or the martensitic phase. For example, when a nickel-titanium alloy is in the form of the R-phase, it may have a lower Young's modulus than when in the austenitic phase. A benefit of a lower Young's modulus is that for a given strain the stress on the device constructed of the material will be less. Therefore, in designing a medical device such as a stent, it may be desirable to produce a stent made from a nickel-titanium including an R-phase so that the stent may have a greater fatigue life or resistance than one not constructed of a nickel-titanium alloy having the R-phase.

It is believed that an article made from a nickel-titanium alloy can be processed to include the R-phase by grinding, cold working, hot working, or a combination thereof. For example, a medical device of a nickel-titanium alloy that includes the R-phase may be formed by selecting a tube or rod made from a nickel-titanium alloy having the austenite phase and a diameter much larger than desired for the final product diameter. A portion of the tube or rod is then ground away until the tube or rod is at the desired diameter. It is believed that by grinding away the outer surface of the tube or rod the Young's modulus of the nickel-titanium alloy forming the tube or rod may be reduced due to transformation of some or substantially all of the austenite to the R-phase.

In another embodiment, grinding and/or pre-conditioning an article made from a nickel-titanium alloy results in formation of the R-phase and produces a ground surface that is substantially free of inclusions and/or substantially free of surface defects. For example, the fatigue life of a member manufactured from a superelastic and/or shape memory alloy can be ground so that the member has at least one cross-sectional dimension (e.g., a thickness or a diameter) in a range from about 0.03 mm to about 0.35 mm, or preferably about 0.05 mm to about 0.3 mm, or more preferably about 0.1 mm to about 0.25 mm. The grinding process may transform some or all of the austenite phase present in the nickel-titanium alloy to the R-phase.

It is surprising and unexpected that reducing the diameter of an article made from a nickel-titanium alloy, such as a wire, can impart greater strength and a significantly increased fatigue life. As mentioned above, it is believed that grinding away the outer surface of a tube or rod lowers the Young's modulus of the material. It is also believed that producing an R-phase material through grinding may increase the fatigue life of an article made from a nickel-titanium alloy by removing a plurality of carbon-based and/or oxide-based inclusions that are near the surface of the article. For example, it is possible that inclusions migrate to the surface of an article such as a wire or tube when the article is being drawn. As discussed previously, inclusions lower the fatigue life of articles made from nickel-titanium alloys by serving as origins for crack formation. Inclusions can also lead to surface defects, which can cause cracking and failure. As such, grinding away the outer surface of a tube or rod increases the fatigue life by removing a plurality of inclusions and surface defects from the surface of the article.

It is further contemplated that the Young's modulus of the material may be altered by applying special heat treatment conditions, cold working, grinding, and/or preconditioning to the nickel-titanium alloy to change the slope of the stress-strain curve, thereby keeping the R-phase of the material at body temperature for a medical device. For example, heat treatment, cold working, grinding, and/or preconditioning can produce an R-phase material with a surface that is work hardened. In another example, heat treatment, cold working, grinding, and/or preconditioning can produce an R-phase material that is stable at body temperature (i.e., stable following implantation into a living, mammalian subject).

III. Methods for Manufacturing Fatigue-Resistant Endoprostheses from Superelastic or Shape-Memory Nickel-Titanium Alloys Various different manufacturing techniques may be used for fabrication of an endoprosthesis according to the present disclosure. In one embodiment, an implantable endoprosthetic device including at least one structural member formed from a fatigue-resistant superelastic or shape-memory nickel-titanium alloy is disclosed. The fatigue-resistant superelastic or shape-memory nickel-titanium alloy may be manufactured according to a method that includes (1) providing a fatigue-resistant superelastic or shape-memory nickel-titanium alloy, (2) forming the nickel-titanium alloy into a first member having a minimum fatigue life defined by survival of at least about 10 million strain cycles at a strain greater than about 0.75%, and (3) assembling at least a portion of an implantable device from the first member in the second state. The method can further include a treating step that includes treating a precursor first member to form the first member, with the first member having a minimum fatigue life defined by survival of at least about 10 million strain cycles at a strain greater than about 0.75%.

1. Providing a Fatigue-Resistant Superelastic or Shape-Memory Nickel-Titanium Alloy The processing of titanium metal typically occurs in 4 steps: reduction of titanium ore into "titanium sponge"; melting of sponge, or sponge plus at least one alloying element to form an ingot; primary fabrication, where an ingot is converted into general mill products such as billet, bar, plate, sheet, strip, and tube; and secondary fabrication of finished shapes from mill products. Providing a fatigue-resistant superelastic or shape-memory nickel-titanium alloy can include selecting/sourcing pure starting materials and/or controlling the purity of the alloy at each of these stages so as to provide a nickel-titanium alloy having an increased fatigue life.

In one embodiment, the providing may include sourcing raw titanium having a reduced oxygen content. Titanium metal cannot be produced by reduction of its dioxide because the metal has a very high affinity for oxygen. As such, titanium metal is typically produced commercially by the Kroll process. In the Kroll process, the oxide form is first converted to chloride through carbochlorination, to make $TiCl_4$. This is condensed and purified by fractional distillation and then reduced with molten magnesium in an argon atmosphere to produce titanium sponge. Nevertheless, titanium sponge tends to contain a high concentration of dissolved and/or chemically bound oxygen due to the titanium's high oxygen affinity.

Because inclusions tend to form in nickel-titanium alloys having a high oxygen concentration, it may therefore be desirable to limit the oxygen content in the titanium sponge below about 200 ppm. For example, by limiting the oxygen content in the titanium sponge to below about 200 ppm, or below about 100 ppm, or below about 50 ppm, the resulting nickel-titanium alloys used to form a medical device may include fewer inclusions, thereby increasing the medical device's fatigue resistance.

In addition to sourcing raw titanium having a low oxygen concentration, it may be possible to reduce the oxygen concentration in nickel-titanium alloys by preparing them in a substantially oxygen free environment. This can have the effect of improving the fatigue life of the resulting alloy. For example, shielding gases, such as argon and/or other inert gases, may be used within the furnace to limit the exposure of the nickel-titanium alloys and elemental constituents thereof to environmental oxygen. Additionally, environmental oxygen may be limited by melting the nickel-titanium alloys and elemental constituents thereof in a vacuum. Furthermore, monitoring of oxygen content and/or partial pressures during melting and/or casting may also facilitate a reduction in inclusions.

The use of a strong oxide former to scavenge free oxygen and/or oxide forming species may be used before and/or during the melting process to reduce the concentration of oxygen in the alloys and reduce the number of inclusions in the nickel-titanium alloys so-formed. For example, the oxide former may be a stronger oxide former than the materials used to produce nickel-titanium alloys. As such, a strong oxide former may be heated in the furnace either before or during preparation of the alloys to scavenge oxygen and oxide forming species from the furnace.

One example of a strong oxide former is titanium metal, which typically forms oxides more readily than a nickel-titanium compound such as NiTi. Titanium metal may be heated and/or melted before and/or during the melting of the alloys to "getter" the furnace. The titanium "getter" scavenges oxygen and oxide forming species from the furnace, thereby reducing inclusion formation in the nickel titanium compound. Other oxide formers may also be used instead of pure titanium.

As discussed in greater detail elsewhere in this application, the presence of carbon-based contaminants can reduce the fatigue life of nitinol and nitinol alloys. For example, the carbon in the carbon-based tooling may be absorbed by the nitinol during the melting process This absorbed carbon can form inclusions, such as titanium carbide, which reduce the fatigue life of articles made from the material. In one embodiment, it may be possible to reduce the amount of carbon to which the nickel-titanium alloys may be exposed by using non-carbon-based tooling in melting an manufacturing processes. Examples of non-carbon-based tooling may include water-cooled copper crucibles for melting, or ceramic or glass crucibles, and/or other tooling.

The carbon and/or oxygen content and or exposure may also be controlled during the other stages of manufacturing. For example, the environment may be controlled during hot working, cold working, heat-treating, and/or other processes to reduce the amount of oxygen and/or carbon that may be introduced into the nickel-titanium alloys.

Similar to the methods for controlling the melting environment, controlling the environment during hot working, cold working, heat treating, and/or other processes may include the use of non-carbon-based tooling, shielding gases, a vacuum, a strong oxide former during the various processes, and/or other controlling steps as generally described above.

For example, during hot and/or cold working, non-carbon-based dies, mandrels, and/or other tooling may be used. In another example, during hot and/or cold working, shielding gases and/or a vacuum may be used to reduce the amount of oxygen to which the nickel-titanium alloys may be exposed. In a further example, the use of a strong oxide former may be incorporated prior to and/or during the processing of nickel-titanium alloys.

In one embodiment, providing a fatigue-resistant superelastic or shape-memory nickel-titanium alloy includes controlling the purity of the material from which the nickel-titanium alloy is produced. As with the embodiments described previously, this can have the effect of increasing the fatigue life of a medical device produced using the nickel-titanium alloy. In one embodiment, controlling the purity of the material from which the alloy is produced may include reducing the ingot size of and/or environmental volume used to produce the nickel-titanium alloy. For example, in vacuum induction melting and vacuum arc re-melting, the nickel-titanium alloys are melted within an environmental volume. Nickel-titanium alloy ingots are typically produced with the mass of about 1000 kg and require an environmental volume of about 150,000 cm$^3$. By reducing the ingot size and/or environmental volume, the oxygen retained within the environmental volume may also be reduced.

In one embodiment, it may be desirable to reduce the ingot mass (and therefore size) from about 1000 kg to about 50 kg. In a further embodiment, it may be desirable to reduce the environmental volume from about 150,000 cm$^3$ to about 7,500 cm$^3$. In these embodiments, the ingot size and environmental volume are reduced by about 20 times. A reduction in ingot size and/or environmental volume by 20 times may proportionally reduce the amount of oxygen that is retained in the ingot by altering the volume to surface area ratio. That is, reducing the volume typically reduces the volume to surface area ratio, which permits conditions such as vacuum melting and shielding gases to more effectively scrub dissolved oxygen from the molten material. Other ingot sizes and or environmental volumes larger and/or smaller than those described above may also be used.

Controlling the purity of the nickel-titanium alloy from which a medical device may be produced may also include removing impurities from the cast nickel-titanium alloys. Inclusions or inclusion forming contaminants may be introduced into the metal during the melting process. The inclusions or inclusion forming contaminants may be distributed unevenly throughout the ingot according to the density of the inclusions and the concentration of oxygen and/or carbon in different zones of the ingot. The use of shielding gasses, non-carbon-based tooling, and/or other processes to limit the number of impurities in a nickel-titanium alloy and/or a radiopaque nickel-titanium alloy may increase the production cost. Thus, removing portions of an ingot where a larger concentration of impurities may be located may be more cost effective than attempting to limit the introduction of impurities during the melting and/or casting process.

Figure 2:
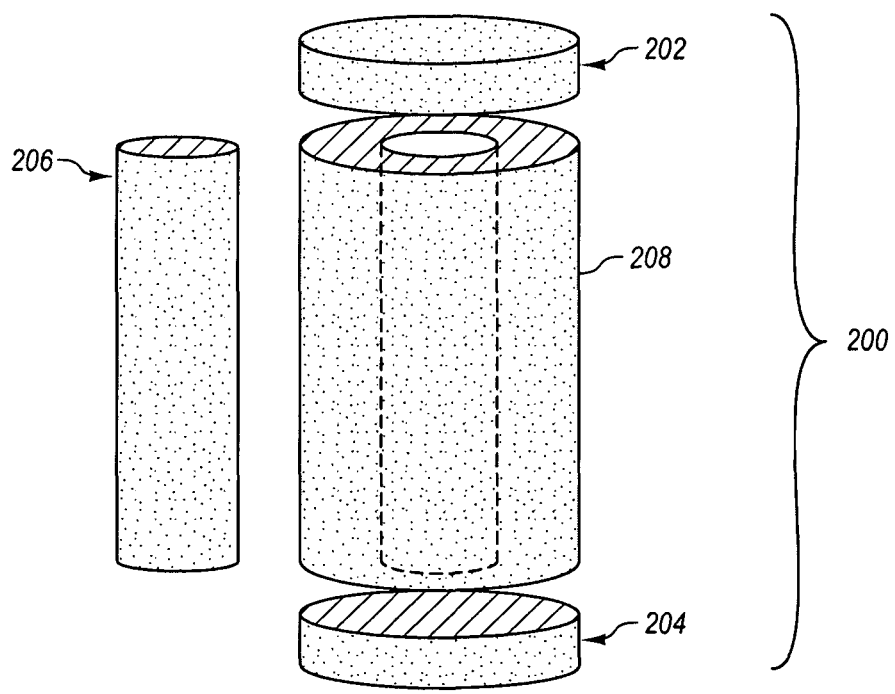
FIG. 2 illustrates an ingot and portions that may be removed in an embodiment of a method for producing a fatigue resistant medical device.

FIG. 2 illustrates the various portions of an embodiment of an ingot 200. The ingot 200 may represent an ingot of a nickel-titanium alloy. In the illustrated configuration, the least dense impurities may be located near an upper portion 202 of the ingot 200 while the densest impurities may be located near a lower portion 204 of the ingot 200. Similarly, as the ingot 200 cools, impurities may gravitate toward the center portion 206 of the ingot 200 due to the zonal exclusion of dissolved oxygen and carbon as the ingot cools. Further, impurities may form on the outer portion 208 of the ingot 200 due to the use of carbon-based tooling during the manufacturing process. It may be possible, therefore, to (i) remove the upper and lower portions of the ingot 200 to remove the least dense and most dense impurities, (ii) remove the center portion 206 of the ingot 200 to remove the impurities at and/or near the center portion 206, and/or (iii) mechanically finish the outer portion 208 to remove surface impurities.

In one embodiment, about 10% of the volume of the ingot 200 may be removed from the upper and lower portions 202, 204, respectively, about 25% of the volume may be removed from the center portion 206, and about 5% of the volume of the ingot 200 may be removed from the outer portion 208. In another embodiment, from about 5% to about 20% of the volume of the ingot 200 may be removed from the upper and the lower portions 202, 204, respectively, from about 5% to about 30% of the volume of the ingot 200 may be removed in the center portion 208, and from about 1% to about 15% of the volume of the ingot 200 may be removed from the outer portion 208.

Another method for providing a fatigue-resistant superelastic or shape-memory nickel-titanium alloy includes inspecting the nickel-titanium alloy for defects prior to using it to fabricate a medical device. This has the advantage of excluding materials from manufacturing processes that could likely produce defective medical devices prior to committing to the time and expense of manufacture and, more importantly, prior to implanting a device in a patient. In one embodiment, a nickel-titanium alloy may be inspected in ingot form, bar/rod form, drawn wire form, tube form, sheet form, formed (i.e., cut to pre-finishing state) form, final form, and/or other forms. While the discussion herein focuses on inspecting materials in the pre-forming stage, one will appreciate that the inspection techniques discussed herein can be used at any stage of manufacture.

Inspecting for defects may include determining the oxygen and/or carbon content of a sample of the nickel-titanium alloys and/or radiopaque nickel-titanium alloys. It may be desirable to test the nickel-titanium alloys and/or radiopaque nickel-titanium alloys in ingot and/or rod form rather than tubing or other forms, because tubing and/or other forms may have more contaminated surfaces than the ingot or rod forms. The contamination may cause inaccurate oxygen and/or carbon content sampling.

The oxygen and/or carbon content of a sample may be determined using Scanning Electron Microscopy (SEM), Energy Dispersive X-Ray Spectroscopy (EDS), Eddy currents, inert gas diffusion, and/or other content determination processes. For example, SEM can be used to determine the oxygen and/or carbon content of a sample by detecting the presence of oxide- or carbide-based inclusions, the presence of which are indicative of an oxygen content in excess of about 200 ppm and/or a carbon content in excess of about 200 ppm. In another example, the oxygen and/or carbon content of a sample may be determined using inert gas fusion based on ASTM Standard E1019-03, which is incorporated herein by reference.

Typically, a sample size of approximately one-half of a percent (0.5%) may be sufficient to determine the oxygen and/or carbon content of a lot. For example, lot sizes of nickel-titanium alloy tubing can be about 1000 tube-feet with a standard length of 18 inches; thus, testing three 18 inch tubes may be sufficient. It will be understood, however, that different lot sizes and different sampling sizes may be possible based upon the particular test result accuracy desired, sampling time available, and other manufacturing and processing factors.

Inspecting for defects may include determining the presence of defects, such as carbide-based and or oxide-based inclusions, voids, surface defects, and/or other defects, in a sample. SEM, EDS, X-Ray with Computed Tomography (CT) technology, ultrasonic technology, and/or other inspection processes may be used to determine the presence of defects.

Typically, SEM can be used to collect images of the surface of a sample. To inspect below the surface, a sample must typically be cut and then examined by SEM and the chemistry of a selected region may be determined using EDS. X-Ray with CT technology devices and ultrasonic technology devices may allow for nondestructive inspection of samples below the surface.

Examples of devices that may use X-Ray with CT technology to determine the presence of defects may include the Micro CT inspection device from Micro Photonic, Inc. or Feinfocus Fox inspection device from Comet GmbH. X-Ray with CT devices may detect defects at a minimum size of about 500 nm (0.5 µm). The X-Ray with CT devices may be used to detect defects in small-dimensioned materials such as wire for guide-wire and hypo-tube for stents and/or other dimensioned materials.

Examples of devices that may use ultrasonic technology to determine the presence of defects may include inspection devices manufactured by SonoScan. Ultrasonic devices may detect defects at a minimum size of about 1000 nm (1.0 µm). The X-Ray with CT devices are typically not used to detect defects in larger dimensioned materials such as ingot, rods, and/or other larger dimensioned materials. Rather, ultrasonic devices may be preferable to detect defects in larger dimensioned materials.

Inspecting for defects may include determining the size of the defects in a sample. SEM, EDS, X-Ray with CT technology, ultrasonic technology, and/or other inspection processes may be used to determine the size and/or composition of any defect. By rejecting samples with defects that are larger than a desired range, the fatigue resistance of the medical device may increase. For example, it may be desirable to reject any material in these processing stages where more than a desired percentage of the defects are larger than a desired size.

In one embodiment, it may be desirable to reject any material in ingot, bar/rod, drawn wire, tube, sheet, formed, final, and/or other forms that has a defect larger than about 5 µm. In some embodiments, it may be desirable to reject any material in these stages where more than about 10% of the defects are larger than about 5 µm. In further embodiments, it may be desirable to reject any material in these stages where more than about 20% of the defects are larger than about 5 µm. In other configurations, the threshold for rejecting materials may be different. For instance, defects larger than 5 µm may be acceptable in certain circumstances, while defects smaller than 5 µm but larger than 1 µm, or some other lower threshold, may be unacceptable. Similarly, the percentage of defects threshold can be greater or lesser than 10%, 20%, or some other percentage.

2. Forming the Fatigue-Resistant Superelastic or Shape-Memory Nickel-Titanium Alloy into a First Structural Member According to the present disclosure, an implantable endoprosthesis includes at least one structural member formed from a fatigue-resistant superelastic or shape-memory nickel-titanium alloy. A method for manufacturing an implantable endoprosthetic device according to the present disclosure includes forming a fatigue-resistant superelastic or shape-memory alloy into a first structural member having a first state. In one embodiment, forming the nickel-titanium alloy into a structural member having a first state can include forming a precursor (e.g., a tube or a wire) having an unfinished physical state that will subsequently be finished to form a part of the completed endoprosthesis. In another embodiment, forming the alloy into a structural member having a first state can include forming a precursor having a first physical state (e.g., a crystalline state) that will be transformed into a second and different physical state in subsequent steps of forming the completed endoprosthesis.

In one embodiment, the forming includes drawing the first member into the formed state. Drawing is a metalworking process that can be used to produce wire or tube that can be used to form at least one structural member of an endoprosthesis. The drawing process is quite simple in concept. The material (i.e., a wire or tube) is prepared by shrinking the beginning of it, by hammering, filing, rolling or swaging, so that it will fit through the die; the material is then pulled through the die. As the material is pulled through the die, its volume remains the same, so the change in diameter is inversely proportional to the change in length. Drawing is usually performed at room temperature and is thus classified as a cold working process, but it may be performed at elevated temperatures according to some embodiments of the present disclosure.

As the drawing die is compressing and elongating the nickel-titanium alloy, the atoms of the nickel-titanium alloy tend to rearrange. For example, drawing a large diameter wire to form a wire having a smaller diameter typically makes the wire stronger and more rigid. In the present context, a drawn wire or tube can be more fatigue resistant. In addition, it is believed that the rearranging and aligning processes that occur as part of the drawing process may cause inclusions in nickel-titanium alloys to migrate to the exterior surface of the drawn wire. This can be advantageous because it allows the removal of fatigue life reducing inclusions, which would otherwise be distributed more-or-less evenly throughout the material, to be removed in subsequent processing steps (e.g., grinding).

In one embodiment, the forming can include work hardening the first member. For example, drawing can include a work hardening effect. Other work hardening processes such as forging can also be included.

In one embodiment, the forming can include annealing the first member. For example, the material can be annealed by heating to a selected temperature either before or after a drawing step.

Various other manufacturing techniques are known and may be used for forming the first structural member of the endoprosthesis. Such manufacturing techniques can be employed to make different elements or sub-elements of the first structural member. For example, the different elements or sub-elements of the first structural member can be formed from a hollow tube using a known technique, such as laser cutting, EDM, milling, chemical etching, hydro-cutting, and the like. Also, the different elements or sub-elements of the first structural member can be prepared to include multiple layers or coatings deposited through a cladding process such as vapor deposition, electroplating, spraying, or similar processes. Also, various other processes can be used such as those described below and or others known to those skilled in the art in light of the teaching contained herein.

Optionally, the different elements or sub-elements of the first structural member can be fabricated from a sheet of suitable material, where the sheet is rolled or bent about a longitudinal axis into the desired tubular shape. Additionally, either before or after being rolled into a tube, the material can be shaped to include elements or sub-elements of the first structural member by being shaped with known techniques such as laser-cutting, milling, etching or the like. If desired, the lateral edges of the structure can be joined together, such as by welding or bonding, to form a closed tubular structure, or the lateral edges can remain unattached to form a coiled, rolled sheet or open tubular structure.

A method of making different elements or sub-elements of the first structural member in accordance with the present disclosure can include sintering sinterable particles to provide a sintered article having the shape of the different elements or sub-elements of the first structural member. The sintering can be conducted in molds that are in the shape of different elements or sub-elements of the first structural member.

In one configuration, the sintered body can be obtained from a molded green body prepared by molding a mixture of sinterable particles with or without a binder into the shape of different elements or sub-elements of the first structural member or body intermediate. Sintering a molded green body that has the shape of different elements or sub-elements of the first structural member can provide a sintered body that can function as an endoprosthesis with no or minimal further processing. Alternatively, after the green body has been formed in the mold and sintered into a hardened element or sub-element of the first structural member, the process can include shaping the sintered body with a stream of energy and/or matter in order to obtain a desired shape. Thus, sintering a green body in a mold can result in an endoprosthesis that is either ready for use, or requires additional processing or finishing.

Additionally, the sintered body can be shaped into an element or sub-element of the first structural member as described herein. Also, the endoprosthesis can be further processed after sintering and/or shaping such as by grinding, sanding, or the like to provide enhanced surface characteristics.

In one embodiment, the forming can further include shaping a nickel-titanium alloy workpiece to form a first structural member. Such shaping techniques can utilize streams of energy and/or streams of matter in order to shape the nickel-titanium alloy workpiece. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the shaping can be designed to direct a stream of energy or a stream of matter at the nickel-titanium alloy to form an endoprosthetic element and/or holes therein.

In one configuration, a stream of energy can cut, shape, and/or form a tube into an endoprostheses by generating heat at the site where the stream intersects the material, as is well known in the art. The thermal interaction can elevate the local temperature to a point, which can cut, melt, shape, and/or vaporize portions of the nitinol and/or a nitinol alloy material from the rest of the material.

Accordingly, one configuration of the stream-cutting apparatus can operate and shape the nitinol and/or a nitinol alloy material by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining.

In one configuration, by knowing the thermal properties of the nickel-titanium alloy, precise energy requirements can be calculated so that the thermal beam provides the appropriate or minimum energy for melting and/or vaporizing the material without significantly melting undesirable portions of the material. For example, laser beams are a common form of a stream of energy that can be used to shape the nickel-titanium alloy. Additionally, there are instances where a laser is preferred over all other cutting techniques because of the nature of the resulting endoprosthesis as well as the characteristics of the nitinol and/or a nitinol alloy material.

In one configuration, a structural member may be manufactured as described herein using a femtosecond laser. A femtosecond laser may be desirable in producing an endoprosthesis because it produces a smaller heat influence zone ("HIZ") or heat affected zone (HAZ) compared to other lasers, or it can substantially eliminate the HIZ or HAZ. In comparison, cutting an endoprosthesis using known methods can result in the tubular material being melted away, and thereby forming the pattern in the tubular member. Such melting can result in embrittlement of some materials due to oxygen uptake into the HIZ.

In one configuration, electrical discharge machining is used to shape nickel-titanium alloy material and/or form holes in the endoprosthetic material as desired. In electrical discharge machining, the main interaction between the stream of energy and the endoprosthetic material is thermal, where heat is generated by producing electrical discharges. This can lead to the nickel-titanium alloy material being removed by melting and evaporation. Some examples of electrical discharge machining include wire electron discharge machining, CNC-controlled electrical discharge machining, sinker electrical discharge machining, small hole discharge machining, and the like.

In another configuration, a charged particle beam can be used for shaping the nitinol and/or a nitinol alloy material, wherein electron beams and ion beams exemplify charged particle beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the green bodies, as described herein. Additionally, there are some instances where electron beams or ion beams are preferred over other cutting techniques.

In one configuration, a stream of chemical matter can be used in order to shape or form holes in the nickel-titanium alloy material. Chemical-jet milling, for example, provides selective and controlled material removal by jet and chemical action. As such, the process is similar to water-jet cutting, which is described in more detail below. In any event, chemical-jet milling can be useful for shaping various types of nitinol and/or a nitinol alloy materials, which provides intricate shaping capabilities.

In another configuration, electrochemical shaping can be based on a controlled electrochemical dissolution process similar to chemical-jet milling a nickel-titanium alloy material. As such, the nickel-titanium alloy material can be attached to an electrical source in order to allow an electrical current to assist in the shaping.

In one configuration, hydro-cutting or water-jet cutting can be used to shape an endoprosthetic material. Hydro-cutting is essentially a water-jet technology that uses the high force and high pressure of a stream of water directed at the endoprosthetic material in order to cut and shape the material as desired. Hydro-cutting can be preferred over some of the other stream-cutting technologies because it can be free of heat, flame, and chemical reactions, and can provide a precise cold shaping technique. Also, heated water with or without being doped with reactive chemicals can also be used.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present disclosure can be used with or without inclusion of such abrasives.

In one configuration, sandblasting, which fits into the regime of stream of matter cutting, can be used to shape a nitinol and/or a nitinol alloy material by projecting a high energy stream of sand particles at the material. Sandblasting cuts materials in a manner similar to hydro-cutting, especially when the water-jet is doped with abrasive particulates. Additionally, various other particulate streams other than sand can be used in the stream-cutting techniques and machinery.

3. Treating a Precursor First Member to Make the First Member

According to the present disclosure, an implantable endoprosthesis includes at least one structural member formed from a fatigue-resistant superelastic or shape-memory nickel-titanium alloy, wherein the at least one structural member is initially formed having a first state and the first state is subsequently transformed to a second state. Transforming the first state to the second state provides minimum fatigue life defined by survival of at least about 10 million strain cycles at a strain greater than about 0.75%.

In one embodiment, transforming the first state into the second state can include finishing a precursor member into a finished member that will be incorporated into a finished endoprosthesis. In another embodiment, transforming the first state into the second state can include transforming a first physical state (e.g., a first crystalline phase) into a second and different physical state (e.g., a second crystalline phase). One will of course appreciate that transforming the first state into the second state can include a mixture of finishing physical transformation steps.

In one embodiment, treating the first member so as to transform the first state into a second state includes grinding the first member so as to reduce at least one dimension of the first member. According to the present disclosure, the fatigue life of the first member may be improved by reducing the dimension of the first member. For example, reducing a dimension of the first member can improve the fatigue life of the first member by removing a plurality of inclusions and/or surface defects that can contribute to fatigue-induced failure of the first member. Reducing a dimension of the first member can also improve fatigue life by lowering the Young's modulus of the material. Lowering the Young's modulus can be advantageous, for example, because the stress on the device constructed of the material will be less is that for a given strain.

Further, reducing a dimension of the first member can improve fatigue life by providing work hardening and/or increase the toughness of an outer surface of the first member.

Reducing a dimension of the first member in the formed state to a reduced state may include grinding the first member into the reduced state. The first member may be ground by centerless and/or other grinding and/or dimension reducing technique. In one embodiment, the first member is reduced by grinding the member to a metal thickness in a range from 0.03 mm to 0.35 mm, more preferably in a range from 0.05 mm to 0.3 mm, and most preferably in a range from 0.1 mm to 0.25 mm. In one embodiment, the first member is a wire and the metal thickness (i.e., the wire diameter) is within one or more of the foregoing ranges.

According to one embodiment, the dimensions of the first member may be determined based on the grain size of the material. In one embodiment, the diameter of the first member may be from about two to about ten times the average grain size of nickel-titanium alloy. For example, if the first member is fabricated from a nickel-titanium alloy having an average grain size of about 15 μm, the first member may have a diameter of from about 30 μm to about 150 μm (i.e., 0.03 mm to about 0.15 mm).

In one embodiment, treating the first member to increase the fatigue life of the material can include work hardening (i.e., cold working), hot working, or heat-treating the material. These process can be used to transform the shape of first member (e.g., reducing a dimension) and/or transform the physical and/or chemical state of the material in the first member.

Work hardening is often produced by the same processes that shape the metal into its final form, including cold rolling and cold drawing. For example, reducing a dimension of the first member can improve fatigue life by providing work hardening and/or increase the toughness of an outer surface of the first member.

Hot working is a metallurgical process where the material (i.e., the alloy) is plastically deformed above its recrystallization temperature. This is important because recrystallization keeps the materials from strain hardening, which ultimately keeps the yield strength and hardness low and ductility high. Hot working can be especially advantageous for shape-memory and superelastic nickel-titanium alloys. For example, if a shape-memory alloy is deformed above its characteristic martensitic start temperature ($M_s$) but below its austenitic finish temperature ($A_f$), the material will return to its original shape when it is warmed again above $A_f$. This property can be exploited, for example, in the manufacture of endoprostheses that adopt a final and pre-determined shape and size upon warming to body temperature. Additional discussion of these phenomena can be found in U.S. Pat. App. Pub. No. 2007/0293939 to Shrivastava et al. entitled "FATIGUE RESISTANT ENDOPROSTHESES," which is incorporated herein by reference in its entirety.

Heat treating is another process that can be used to transform the material used to form the first member from the first state to the second state. Heat treatment involves the use of heating or chilling, normally to extreme temperatures, to achieve a desired result such as hardening or softening of a material. The first member or portions thereof can be selectively hardened or softened to increase the fatigue life of the first member. Heat treatment techniques include annealing, tempering and quenching, and precipitation strengthening. It is noteworthy that while the term heat treatment applies only to processes where the heating and cooling are done for the specific purpose of altering properties intentionally, heating and cooling often occur incidentally during other manufacturing processes such as hot forming or welding.

Annealing is a technique used to recover cold work and relax stresses within a metal. Annealing typically results in a soft, ductile metal. During annealing, small grains formed in processes such as cold working recrystallize to form larger grains.

To harden by tempering and quenching, a metal is typically heated into the austenitic crystal phase and then quickly cooled. Depending on the alloy and other considerations (such as concern for maximum hardness vs. cracking and distortion), cooling may be done with forced air or other gas (such as nitrogen), oil, polymer dissolved in water, or brine. Upon being rapidly cooled, a portion of austenite (dependent on alloy composition) will transform to martensite.

To harden by precipitation hardening, a metal (usually an alloy) is heated and then quenched such that the some of the alloying elements are trapped in solution. In subsequent "aging," the alloying elements diffuse through the microstructure and form intermetallic particles. These intermetallic particles nucleate and fall out of solution and act as a reinforcing phase, thereby increasing the strength of the alloy. Some alloys may age "naturally" meaning that the precipitates form at room temperature, or they may age "artificially" when precipitates only form at elevated temperatures.

The minimum fatigue life of articles manufactured from nickel-titanium alloys can also be increased by treating the first member to produce an R-phase material. The R-phase of a superelastic nickel-titanium alloy is a transformation state between an austenitic phase and a martensitic phase that occurs as a result of the application of stress or another force at a temperature below the martensite start temperature.

Superelastic and/or shape memory nickel-titanium alloys in the R-phase can have a significantly longer fatigue life than materials in either the austenitic state or the martensitic state. For example, when a material is within its R-phase, the material may and can have a lower Young's modulus than when in the austenitic phase. A benefit of a lower Young's modulus is that for a given strain the stress on the device constructed of the material will be less. Therefore, in designing a medical device such as a stent, it may be desirable to produce a stent made from a nickel-titanium alloy that includes the R-phase so that the stent has a greater fatigue life or resistance than one not constructed of a nickel-titanium alloy including the R-phase.

It is believed that an R-phase of a nickel-titanium alloy can be made using processes such as grinding, cold working, hot working, or a combination thereof. For example, it may be possible to construct a medical device made from a nickel-titanium alloy including such an R-phase material by selecting a tube or rod from which the medical device will be constructed having a diameter much larger than desired for the final product diameter. A portion of the tube or rod is then ground away until the tube or rod is at the desired diameter. It is believed that by grinding away the outer surface of the tube or rod, the R-phase of the nickel-titanium alloy may be formed in an outer region the tube or rod while an inner core remains in the austenite phase unaffected by the grinding operation. Such outer region extends inwardly from the ground surface and may have an indeterminate shape. Consequently, the Young's modulus of the nickel-titanium alloy may be locally reduced in the outer region due to the presence of the R-phase thereby enhancing fatigue resistance. In some embodiments, the grinding process may be sufficient so that the austenite is transformed to the R-phase throughout the tube or rod.

In another embodiment, grinding and/or pre-conditioning the nickel-titanium alloy to produce the R-phase produces a ground exterior surface that is substantially free of inclusions and/or substantially free of surface defects. For example, the fatigue life of a member manufactured from a superelastic and/or shape memory nickel-titanium alloy can be increased by the presence of the R-phase with a ground surface and the member having at least one cross-sectional dimension (e.g., a thickness or diameter) in a range from about 0.03 mm to about 0.35 mm, or preferably about 0.05 mm to about 0.3 mm, or more preferably about 0.1 mm to about 0.25 mm.

It is further contemplated that the Young's modulus of the material may be altered by applying special heat treatment conditions and/or cold working and/or grinding or preconditioning to the material to change the slope of the stress-strain curve. For example, pre-fatiguing a superelastic or shape-memory nickel-titanium alloy can produce a fatigue-resistant R-phase by causing a stress-induced transformation from an austenitic phase to a more fatigue-resistant R-phase. The pre-fatiguing may transform only a portion of or substantially all of the austenite to the R-phase.

4. Assembling an Implantable Device

According to the present disclosure, an implantable endoprosthesis that includes the first member formed from a fatigue-resistant superelastic or shape-memory alloy in the second state can be assembled. Assembling can include processes such as additional shaping of the first member, additional cutting of the first member using laser cutting, waterjetting cutting, milling, turning, and/or other forming techniques. In another example, the implantable device may be formed by connecting at least two portions of the first member. The two portions may be connected by welding, adhesive bonding, and/or other connecting processes.

Assembling an endoprosthesis can also include one or more surface finishing processes. Providing a defect-free surface has been found to important for imparting an improved fatigue life. For example, surface finishing process can remove a plurality of defects (e.g., microcracks) and/or inclusions from the surface of the endoprosthesis. Removing defects and inclusions from the surface of the endoprosthesis improves fatigue life by inhibiting certain fatigue-induced failure modes. Suitable surface finishing processes according to the present disclosure include, but are not limited to, electropolishing, bead blasting, tumbling, grinding, laser energy finishing, and/or other mechanical finishing processes.

For some alloys and endoprostheses it may be particularly advantageous to combine a mechanical finishing step, such as grinding, with a chemical finishing step such as electropolishing. For example, it has been found that nickel-titanium alloys such as a Ni—Ti—Pt alloy are particularly difficult to finish by electropolishing. Endoprostheses and portions of endoprostheses made from a Ni—Ti—Pt alloy can be provided with a substantially defect-free surface using grinding, while a subsequent electropolishing step can provide a Ti rich surface for passivation.

Implantable devices may include endoprosthesis, drug delivery stents, drug delivery catheters, stent-grafts, grafts, drug delivery balloons, guidewires, orthopedic implants, PFO closure devices, pacemaker leads, dental implants, fixation screws, indwelling catheters, implantable filters, ocular implants, pharmacotherapeutic implants, blood-contacting components of extracorporeal devices, staples, filters, needles, tubes, coils, wires, clips, screws, sensors, plates, conduits, portions thereof, combinations thereof, and/or other implantable devices.

Figure 3:
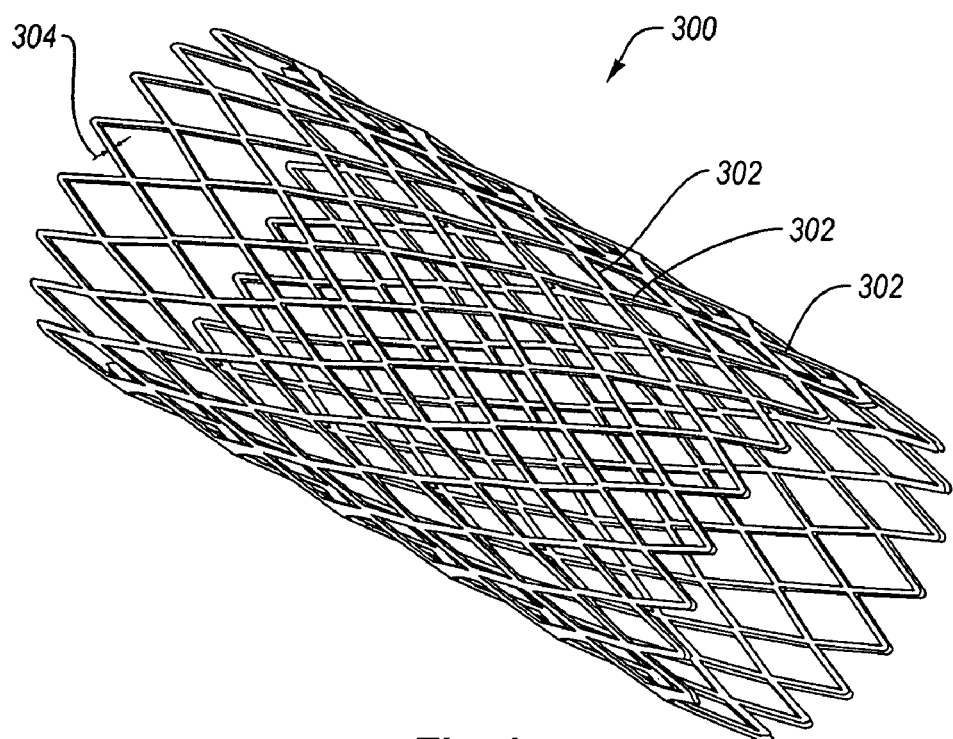
FIG. 3 illustrates an embodiment of a stent, in accordance with the present disclosure.
Figure 4:
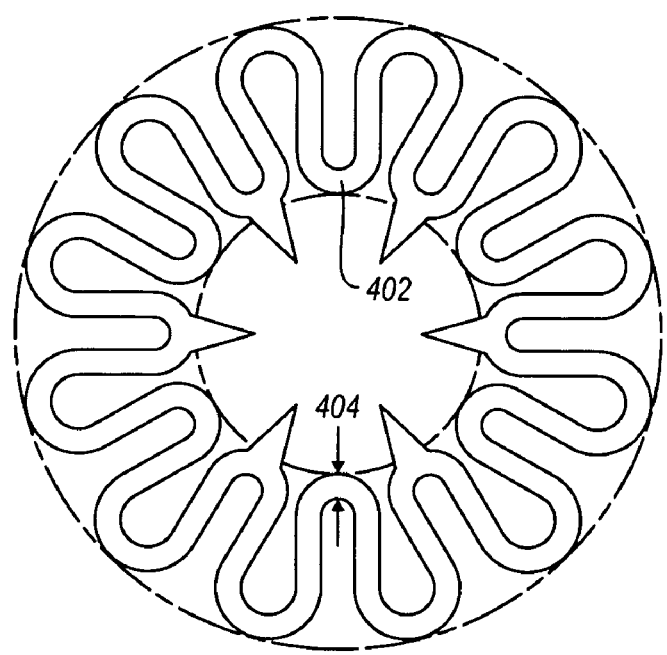
FIG. 4 illustrates an embodiment of a closure element, in accordance with the present disclosure.

Some medical devices, such as stents 300 and/or closure elements 400, may include struts 302, 402, as shown in FIGS. 3 and 4. These struts 302, 402 may have a diameter 304, 404 and/or other predetermined dimensions. In one embodiment, the struts 302, 402 may have a diameter 304, 404 and/or other predetermined dimensions in a range from 0.03 mm to 0.35 mm, more preferably in a range from 0.05 mm to 0.3 mm, and most preferably in a range from 0.1 mm to 0.25 mm. In another embodiment, the diameter 304, 404 of the struts 302, 402 may be from about two to about ten times the grain size of a radiopaque Nitinol alloy. For example, if the grain size of a radiopaque Nitinol alloy were about 15 µm, the strut 302, 402 may be from about 30 to about 150 µm in diameter 304, 404. Rather than the diameter of the struts 302, 402 being about two to about ten times the grain size of a radiopaque Nitinol alloy, it will be understood that in other configurations any dimension of the strut or member of the implantable device can be about two to about ten times any corresponding dimension of the grain size of a nickel-titanium alloy.

IV. Methods for Delivering an Endoprosthesis

Generally, endoprostheses of the present disclosure can be delivered into a body of a subject by any method known or developed. For example, the method of using catheters to deploy self-expandable or balloon-expandable stents can be employed.

In one embodiment, endoprostheses of the present disclosure are configured for use in a body lumen. As such, the present disclosure includes a method of delivering an endoprosthesis into a body lumen of a subject. Such a method includes: (1) providing an endoprosthesis as described herein, (2) orienting the endoprosthesis into a delivery orientation with a cross section that is smaller than the body lumen, (3) inserting the endoprosthesis in the delivery orientation into a delivery device, such as a delivery catheter that can be configured substantially as a catheter for delivering a stent, (4) delivering the endoprosthesis to a desired deployment site within the body lumen of the subject, (5) removing the endoprosthesis from the delivery device, and (6) expanding the endoprosthesis so as to have an enlarged dimension that applies radial forces to an inner wall of the body lumen.

Figure 5A:
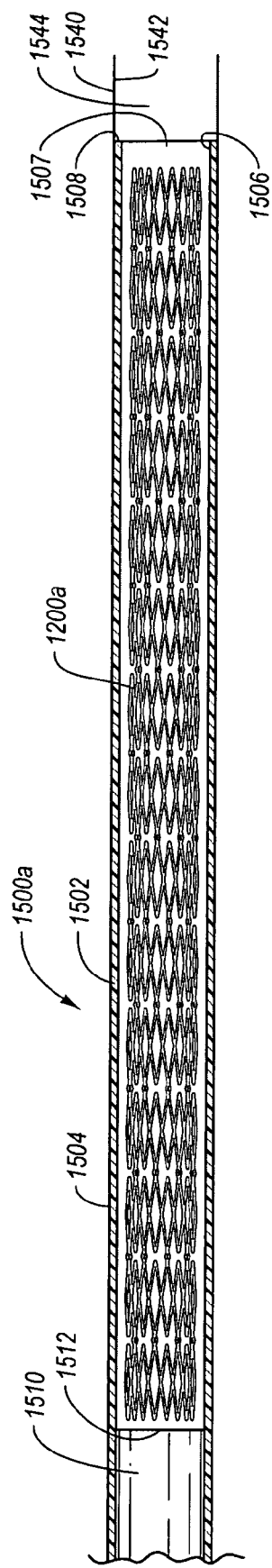
FIGS. 5A and 5B illustrate a method for implanting an endoprosthesis.
Figure 5B:
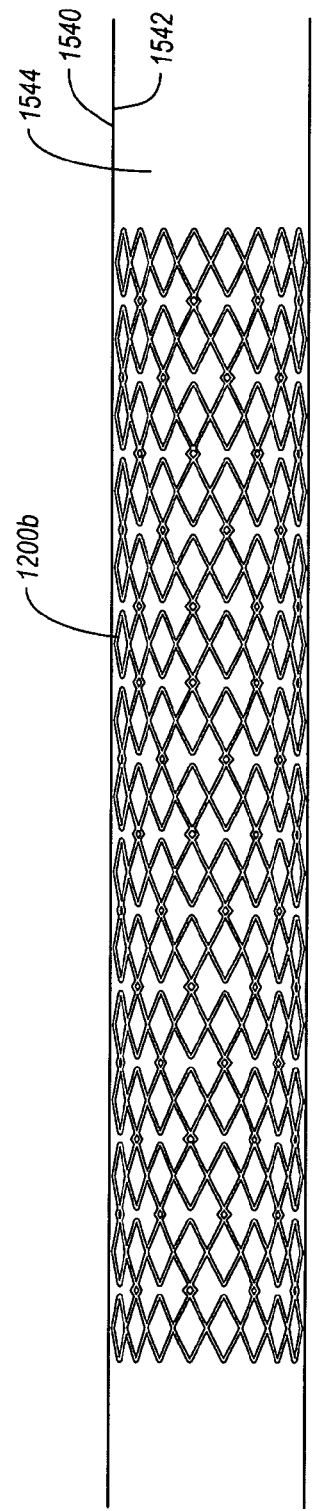

FIGS. 5A-5B are side views illustrating an embodiment of an endoprosthesis and methods of deploying such an endoprosthesis into a body lumen in accordance with the present disclosure.

FIG. 5A is a schematic representation illustrating a delivery system 1500a for delivering an endoprosthesis 1200a into a body lumen 1540, such as a blood vessel like the vena cava. The delivery system includes an endoprosthesis delivery catheter 1502 configured for delivering a hybrid segmented endoprosthesis 1200a that is retained by the catheter 1502 in a delivery orientation (e.g., radially compressed). The delivery catheter 1502 includes a delivery member 1504 that defines a delivery lumen 1507 that is shaped and dimensioned to retain the endoprosthesis 1200a in the delivery orientation. Accordingly, the delivery member 1504 is substantially tubular and configured similarly as any delivery catheter member. An internal surface 1506 defined by the delivery member 1504 holds the endoprosthesis 1200a within the delivery catheter 1502.

The delivery system 1500 delivers the endoprosthesis 1200a with a catheter 1502 similarly to the method of delivering other endoprostheses into a body lumen. As such, an insertion site (not shown) is formed through the skin (not shown) that traverses into a body lumen 1540. A guidewire (not shown) is then inserted through the insertion site, through the body lumen 1540, to the delivery site 1544. A catheter (not shown) is then inserted into the body lumen 1540 to the delivery site 1544 over the guidewire, and the guidewire is optionally extracted. The delivery catheter 1502 is then inserted through the catheter (not shown) until reaching the delivery site 1544 and the catheter is withdrawn.

Optionally, the catheter is the delivery catheter 1502, and in this instance, the delivery catheter 1502 is retained at the delivery site 1544 and the endoprosthesis 1200a is delivered to the delivery site 1544 through the lumen 1507 of the delivery catheter 1502. A pusher 1510 can be used to push the endoprosthesis 1200a within the lumen 1507 of the delivery catheter 1502 to the delivery site 1544.

Accordingly, the delivery system 1500 is inserted through percutaneous insertion site (not shown) that traverses from the skin (not shown) into the body lumen 1540 until reaching the delivery site 1544. The pusher 1510 includes a distal end 1512 that pushes the endoprosthesis 1200a from the distal end 1508 of the delivery member 1504. Alternatively, the endoprosthesis 1200a can be disposed at the distal end 1508 of the delivery member 1504, and the pusher 1510 holds the endoprosthesis 1200a at the delivery site 1544 and the delivery member 1504 is retracted over the endoprosthesis 1200a and pusher 1510. Thus, the pusher 1510 can push the endoprosthesis 1200a from the delivery catheter 1502 or the delivery member 1504 can be withdrawn over the endoprosthesis 1200a and pusher 1510 in order to deploy the endoprosthesis 1200a.

FIG. 5B illustrates the endoprosthesis 1200b in the deployed configuration at the delivery site 1544 within the body lumen 1540. As such, the endoprosthesis 1200b is radially expanded so as to contact the inner wall 1542 of the body lumen 1540.

In one embodiment, the present disclosure can include a method of extracting an endoprosthesis from a body lumen, which can include: (1) inserting an endoprosthesis-extracting medical device into the body lumen so as to come into contact with an endoprosthesis, (2) engaging the endoprosthesis-extracting medical device with the endoprosthesis, (3) radially compressing the endoprosthesis so as to have a reduced dimension with a cross section that is smaller than the body lumen; and retrieving the endoprosthesis from the desired deployment site within the body lumen of the subject. Optionally, the endoprosthesis can be received into the endoprosthesis-extracting medical device, which can be substantially similar to a catheter.

In one embodiment, at least one of delivering or retrieving the endoprosthesis is performed with a catheter. Catheters configured for delivering and/or retrieving endoprostheses from a body lumen can be adapted for delivering and/or retrieving the endoprosthesis of the present disclosure.

V. Examples

Example 1

In Example 1, nitinol (NiTi) and a radiopaque nitinol (R-nitinol) alloy (NiTiPt) wire samples (manufactured by Fort Wayne Metals) were used to study the differences in fatigue life between NiTi and NiTiPt. The NiTi and NiTiPt wires were approximately 40% cold worked and heat-treated and straightened with an $A_f$ temperature of approximately 8° C. (bend and free recovery method).

The composition of the nitinol was 50.8% nickel and 49.2% titanium. The R-nitinol used in this study included 43% nickel, about 49.5% titanium, and about 7.5% platinum. The wire specimens were drawn to an initial diameter of 0.343 mm, hand-sanded with sandpaper, and electropolished using hydrochloric acid and nitric acid. The final diameter of the electropolished nitinol and R-nitinol specimens was 0.300 mm and 0.280 mm, respectively.

To illustrate differences between NiTi and NiTiPt alloy wires, were subjected to fatigue testing and failure analysis. Fatigue testing was performed on NiTi and NiTiPt wire samples using a rotating beam apparatus as illustrated in FIG. 1. Failure analyses were performed on samples that failed fatigue testing by photographing and analyzing the fracture origins and outer surfaces of the wires using SEM. Furthermore, inclusions found at the fatigue origins were analyzed using EDS and the semi-quantitative analysis.

Nitinol (NiTi) and nickel-titanium-platinum (NiTiPt) alloy wire samples were subjected to alternating of about 0.75%, about 0.85%, about 0.95%, about 1.05%, about 1.15%, and about 1.25%. A minimum often (10) samples of nitinol and R-nitinol were fatigue tested for each strain.

Figure 6:
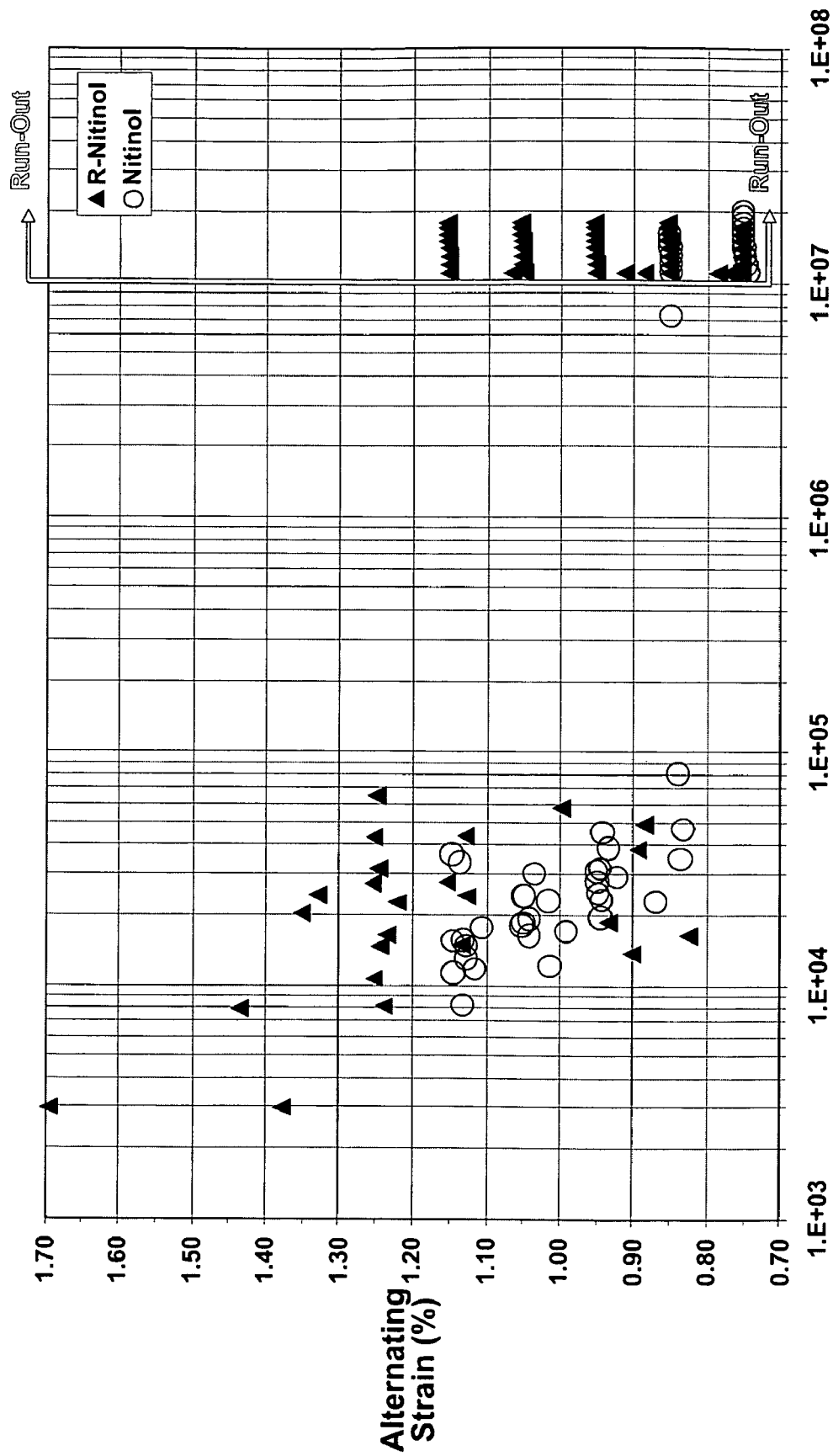
FIG. 6 illustrates a stress-strain plot comparing the fatigue life of nitinol to radiopaque nitinol, tested using an apparatus as illustrated in FIG. 1.

Representative data comparing NiTi to NiTiPt are shown in FIG. 6. In FIG. 6, each solid dot represents one data point. All data points staying on the right side of the "Run-Out" line survived after 10 million cycles. The fatigue test was stopped when the specimen passed the 10 million cycles.

Generally, the number of cycles to failure decreases as the strain increases. Nevertheless, bimodal regions can be seen for NiTi and NiTiPt samples where, at the same strain, some specimens survive and other specimens fail. For NiTi specimens, the strain groups were 0.75% and 0.85%; for NiTiPt specimens, strain groups can be seen at 0.75%, 0.85%, 0.95%, 1.05%, and 1.15%. These data indicate that the fatigue resistance of NiTiPt is generally superior to NiTi.

Fractured specimens in the bimodal region of the S-N curve were examined under a SEM. There were inclusions and surface defects found at some of the fracture origins and a HITACHI Model S-4300 FE-SEM equipped with EDS was utilized to determine the composition of the inclusions.

Analyses on the failed samples in the bimodal region for NiTi and NiTiPt indicate that the bulk of failures are caused by surface defects, such as microcracks, and the presence of inclusions. Analysis of the failed specimens in the bimodal region indicates that 90% of the failed NiTiPt wire samples had $Ti_4(NiPt)_2O_x$ or $Ti_4Ni_2O_x$ inclusions ranging in size from about 4 to about 17 μm, while 1 NiTi sample failed because of a TiC inclusion.

Probabilities of fracture for NiTi and NiTiPt at the tested strains were calculated. The probability of fracture is defined according to Formula 2:

$$P = \frac{(3r-1)}{3n+1} \times 100\%$$ Formula 2

Where 'r' is the number of fractured specimens and 'n' is the total number of tested specimens within the range of strain. The probability of fracture is calculated and summarized in Table 1.

TABLE 1

Probability of fracture for R-nitinol and nitinol specimens

| Alternating Strain (%) | R-Nitinol (NiTiPt) | | | Nitinol (NiTi) | | |
|---|---|---|---|---|---|---|
| | n | r | P (%) | n | r | P (%) |
| 0.71~0.80 | 11 | 0 | 3 | 10 | 0 | 3 |
| 0.81~0.90 | 13 | 4 | 27 | 11 | 5 | 41 |
| 0.91~1.00 | 11 | 2 | 15 | 10 | 10 | 94 |
| 1.01~1.10 | 9 | 0 | 4 | 9 | 9 | 93 |
| 1.11~1.20 | 12 | 4 | 30 | 10 | 10 | 94 |
| 1.21~1.30 | 9 | 9 | 93 | N/A | N/A | N/A |

Fatigue testing and failure analyses indicate that fatigue resistance for radiopaque nitinol is generally superior to nitinol. For example, the probability of fracture is about 21% for R-nitinol versus about 41% in the range of transition (0.75%~1.15% for R-nitinol vs. 0.75%~0.85% for nitinol). The maximum strain for radiopaque nitinol wire is about 1.5 times the maximum strain for nitinol wire after 10 million cycles (i.e., R-nitinol wire can survive for 10 million cycles at a strain of about 1.15% versus survival of a strain of about 0.85% for nitinol). Furthermore, many of the failures of the radiopaque nitinol and/or nitinol samples appear to be due to $Ti_4(NiPt)_2O_x$ or $Ti_4Ni_2O_x$ inclusions, indicating that the fatigue resistance of R-nitinol and nitinol can be significantly improved by reducing the amount of inclusions.

Example 2

In Example 2, radiopaque nitinol (R-nitinol) alloy (NiTiPt) wire samples that failed due to the presence of inclusions were excluded from calculations to study the differences in fatigue life between NiTi and inclusion-free NiTiPt. The data summarized in Table 1 suggests that $Ti_4(NiPt)_2O_x$ inclusions appear in the NiTiPt inconsistently. For example, NiTiPt wire has a bifurcated failure probability with similar failure probabilities appearing at a strain of about 0.75% and a strain of about 1.05%. It is believed that NiTiPt failures at low strain are caused by inclusions, while the higher strain limit of 1.05% is more representative of the true potential of NiTiPt.

Figure 7:
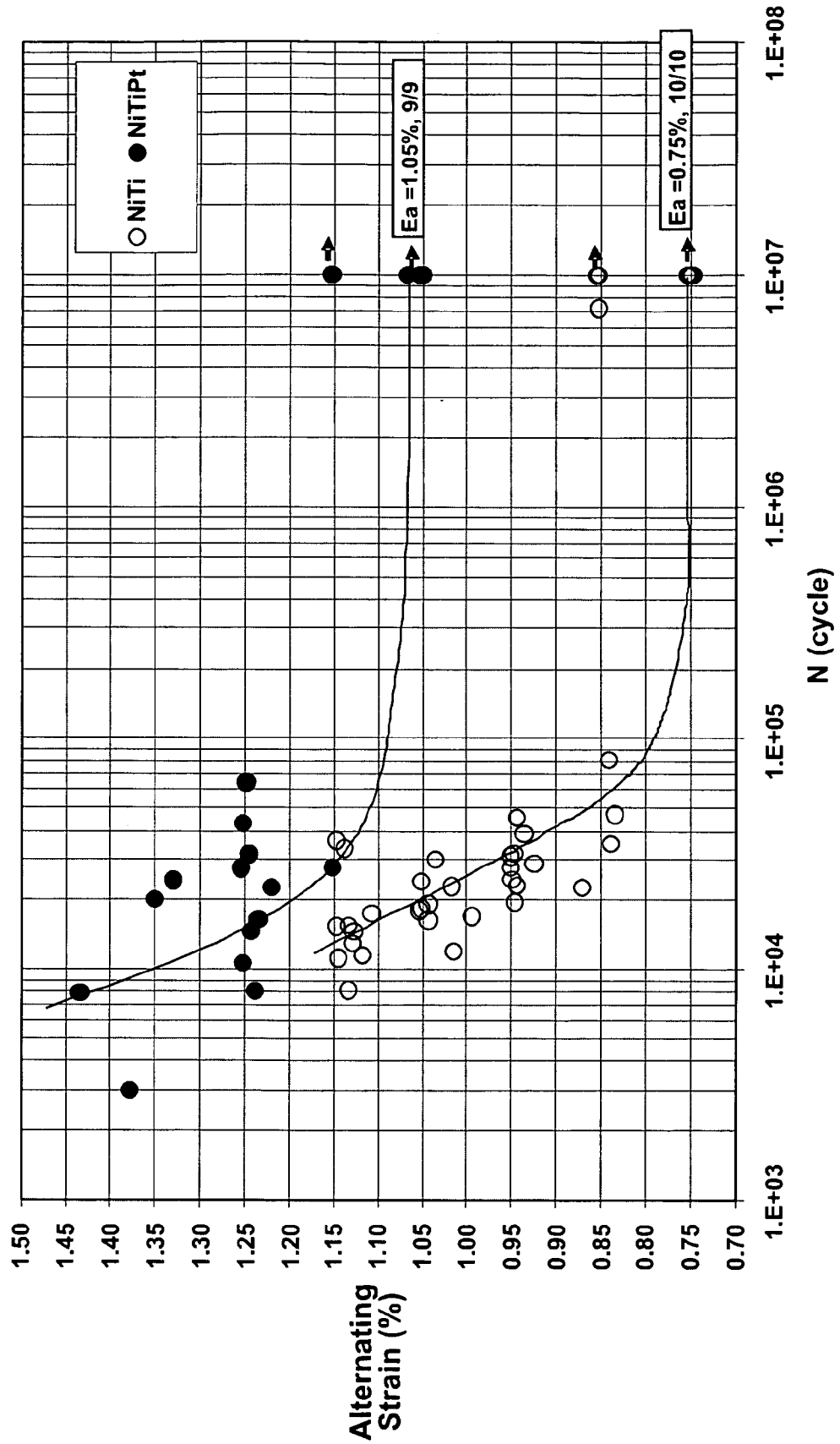
FIG. 7 illustrates a stress-strain plot comparing the fatigue life of nitinol to radiopaque nitinol, tested using an apparatus as illustrated in FIG. 1.

In order to test this hypothesis, samples from the group in Example 1 having $Ti_4(NiPt)_2O_x$ inclusions at the fracture origin are excluded from calculations and the date were re-plotted in FIG. 7. For NiTi specimens, the predominant strain group can be seen at 0.75%; for NiTiPt specimens, the predominant strain group can be seen at 1.05%. These data indicate that the fatigue resistance of NiTiPt is generally superior to NiTi and that the fatigue resistance of NiTiPt can be significantly improved by limiting the oxygen content of the alloy, which can reduce the incidence of $Ti_4(NiPt)_2O_x$ in NiTiPt. One can also reasonably conclude based on these data that the fatigue resistance of that the fatigue resistance of nitinol (i.e., NiTi) and other nickel-titanium alloys (e.g., NiTiPt) can be improved by limiting the oxygen content in the alloy.

Example 3

In Example 3, nitinol (NiTi) and a radiopaque nitinol (R-nitinol) alloy (NiTiPt) wire samples were used to study the differences in fatigue life between NiTi and NiTiPt as a function of surface finish. Table 2 summarizes the various wire samples used in these experiments.

TABLE 2

| Name | Material | Wire OD | Surface Finish |
|---|---|---|---|
| NiTiPt Large | NiTiPt Alloy | 0.343 mm | Drawn/HT |
| | | 0.305 mm | Insuff-EP |
| | | 0.279 mm | EP |
| NiTi Large | NiTi Alloy | 0.343 mm | Drawn/HT |
| | | 0.305 mm | EP |

Figure 8:
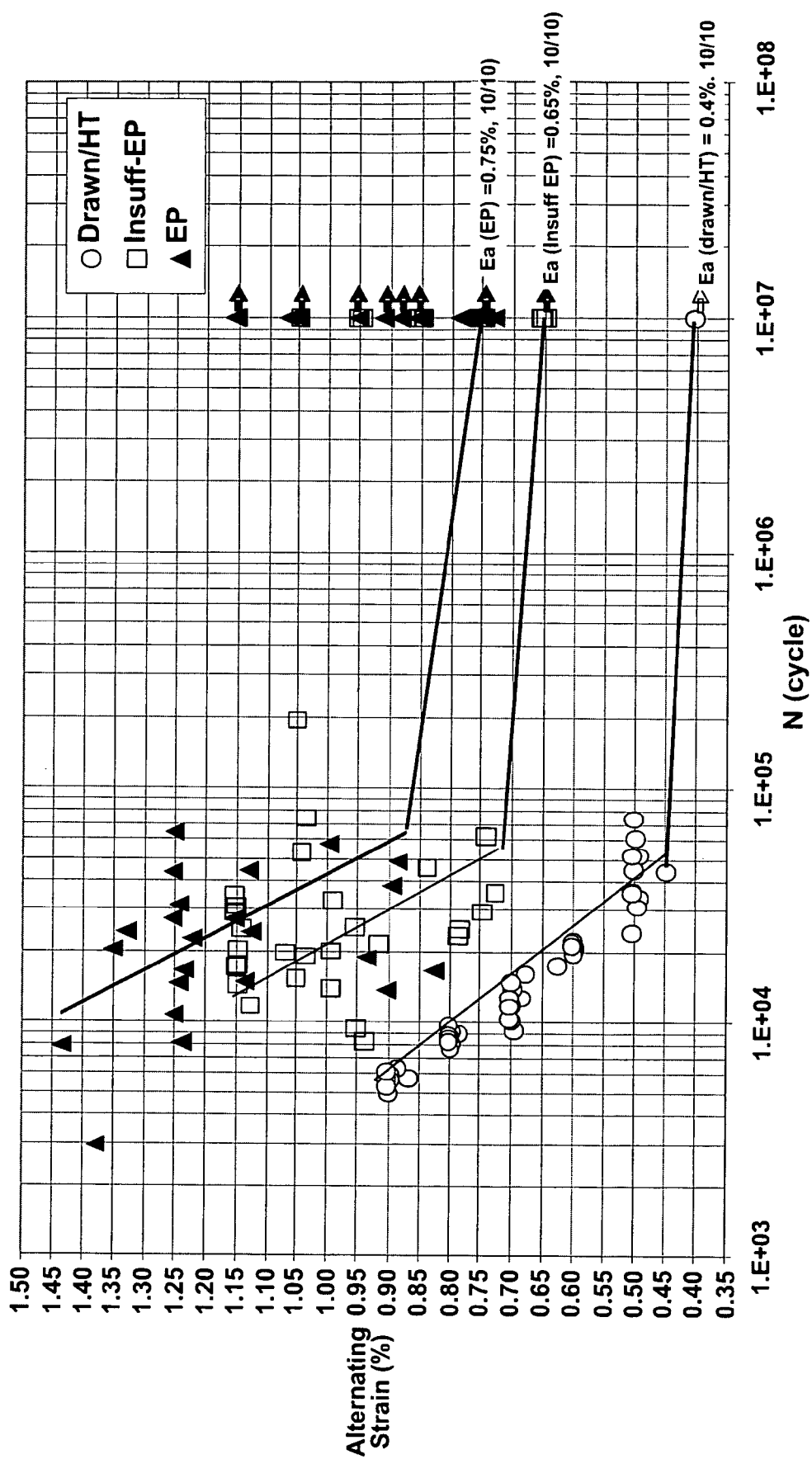
FIG. 8 illustrates a stress-strain plot comparing the fatigue life of samples of a radiopaque nitinol alloy (NiTiPt) as a function of different surface treatments, tested using an apparatus as illustrated in FIG. 1.
Figure 9:
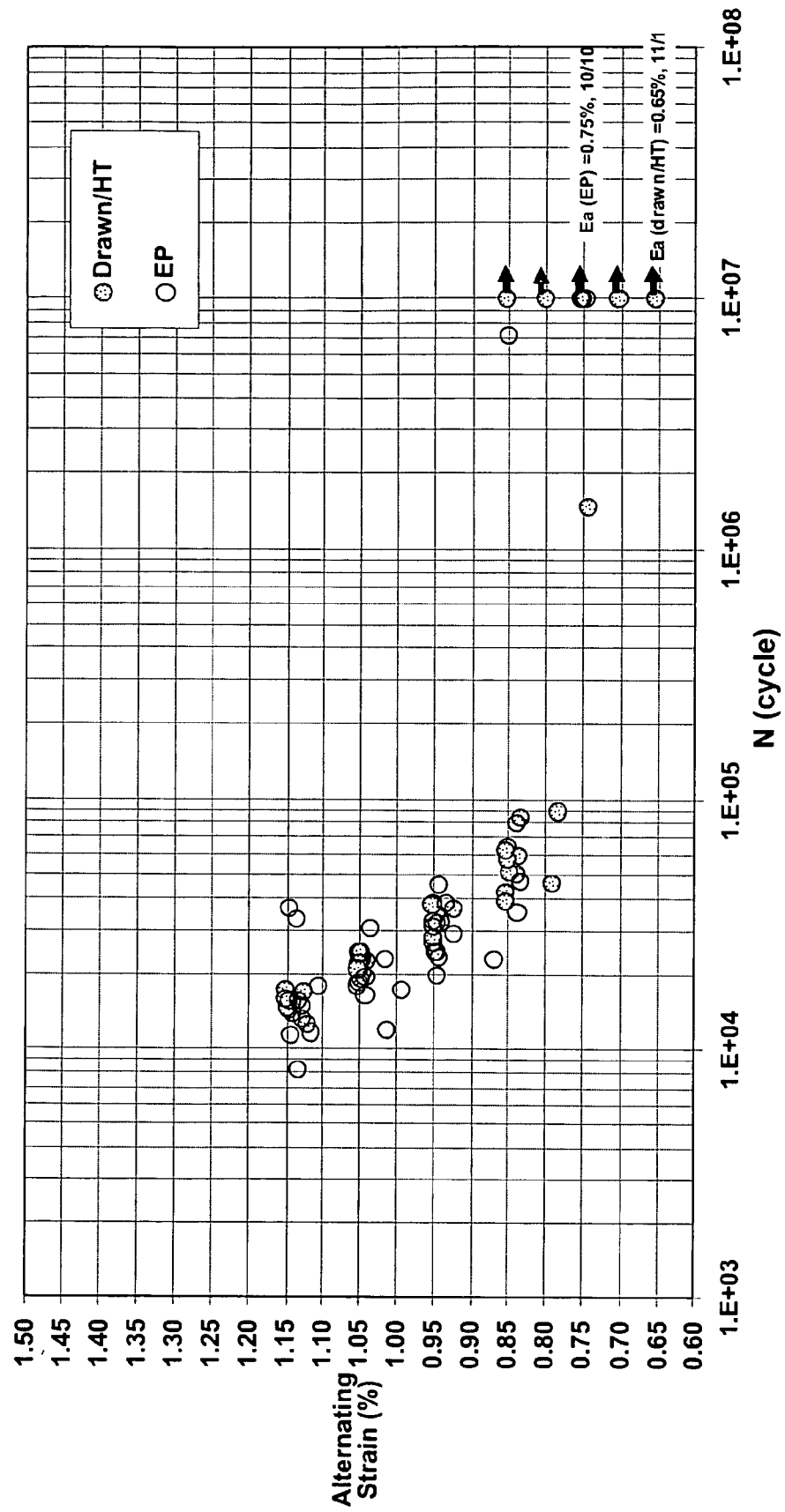
FIG. 9 illustrates a stress-strain plot comparing the fatigue life of samples of nitinol (NiTi) as a function of different surface treatments, tested using an apparatus as illustrated in FIG. 1.

Data comparing surface treatments for NiTiPt (drawn/HT vs. insufficient electropolish vs. electropolish) and NiTi (drawn/HT vs. electropolish) are depicted in FIGS. 8 and 9. These data clearly show that the fatigue life of NiTiPt and NiTi materials is improved by having a defect-free surface, such as that provided by electropolishing and other surface treating techniques discussed herein. In particular, the fatigue life of articles made from NiTiPt, a nitinol alloy that is known to be difficult to electropolish, can be improved by having a surface that is a completely electropolished.

As depicted in FIGS. 8 and 9, the NiTiPt endurance fatigue strain limit was improved by 88% after complete electropolishing. For NiTi, the endurance fatigue strain limit was improved by 15% after electropolishing.

Electropolishing may improve the fatigue life of NiTiPt and NiTi by at least one of two possible mechanisms. For example, many test samples failed because of microcracks and other surface defects. Electropolishing, which removes a thin layer of material from the surface that is polished, likely removes the layer of material that includes the cracks leaving a defect-free surface. By a similar phenomenon, electropolishing can likely remove a thin outer layer from the NiTiPt and/or NiTi that includes carbide and/or oxide impurities.

Example 4

In Example 4, nitinol (NiTi) and a radiopaque nitinol (R-nitinol) alloy (NiTiPt) wire samples were used to study the fatigue life of NiTi and NiTiPt as a function of wire diameter. Table 2 summarizes the various wire samples used in these experiments.

TABLE 3

| Name | Material | Wire OD | Surface Finish |
|---|---|---|---|
| NiTiPt Large | NiTiPt Alloy | 0.343 mm | Drawn/HT |
|  |  | 0.305 mm | Insuff-EP |
|  |  | 0.279 mm | EP |
| NiTiPt Small |  | 0.127 mm | Ground |
| NiTi Large | NiTi Alloy | 0.343 mm | Drawn/HT |
|  |  | 0.305 mm | EP |
| NiTi Small |  | 0.127 mm | Ground |

Figure 10:
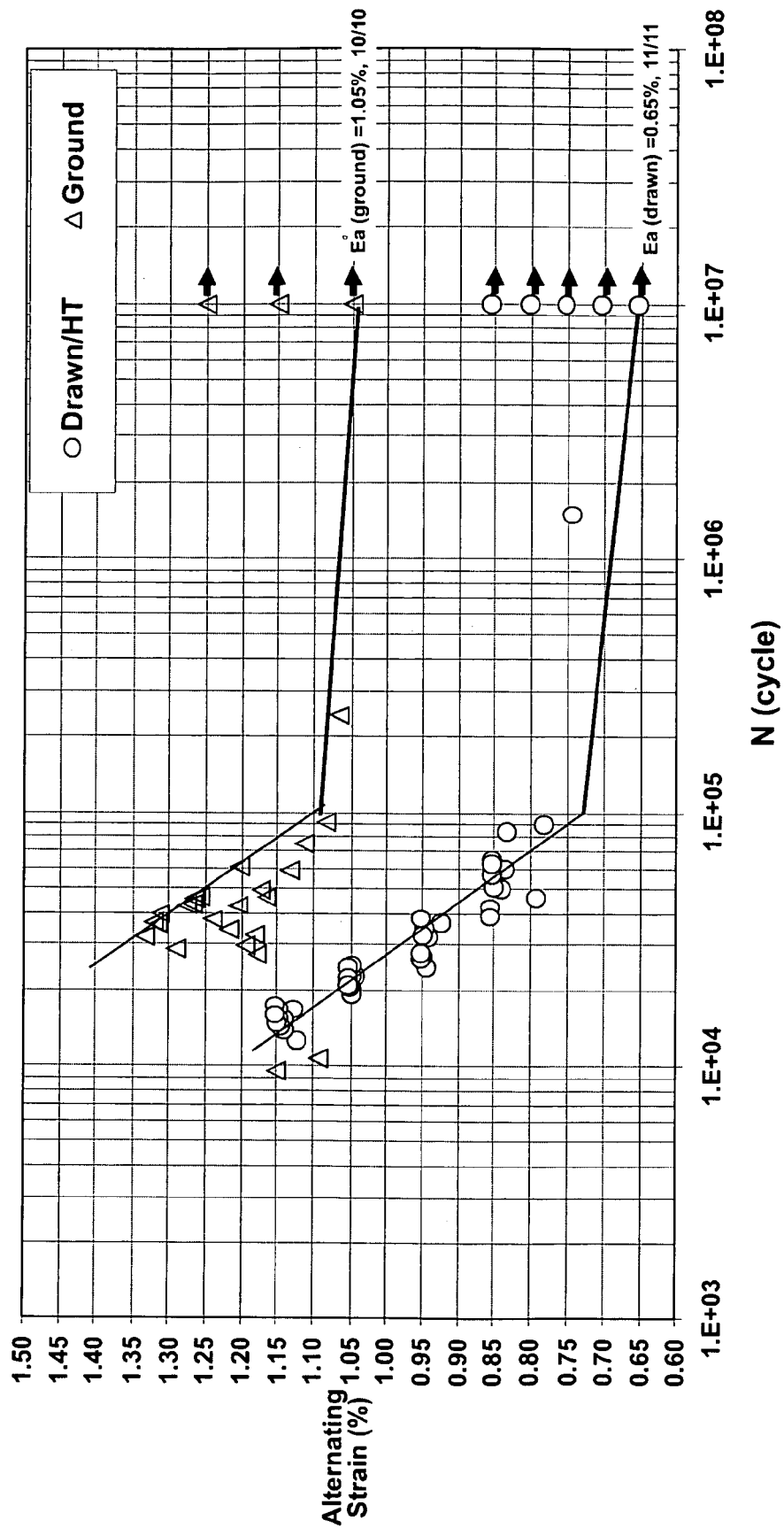
FIG. 10 illustrates a stress-strain plot comparing the fatigue life of samples of nitinol (NiTi) as a function of wire diameter, tested using an apparatus as illustrated in FIG. 1.
Figure 11:
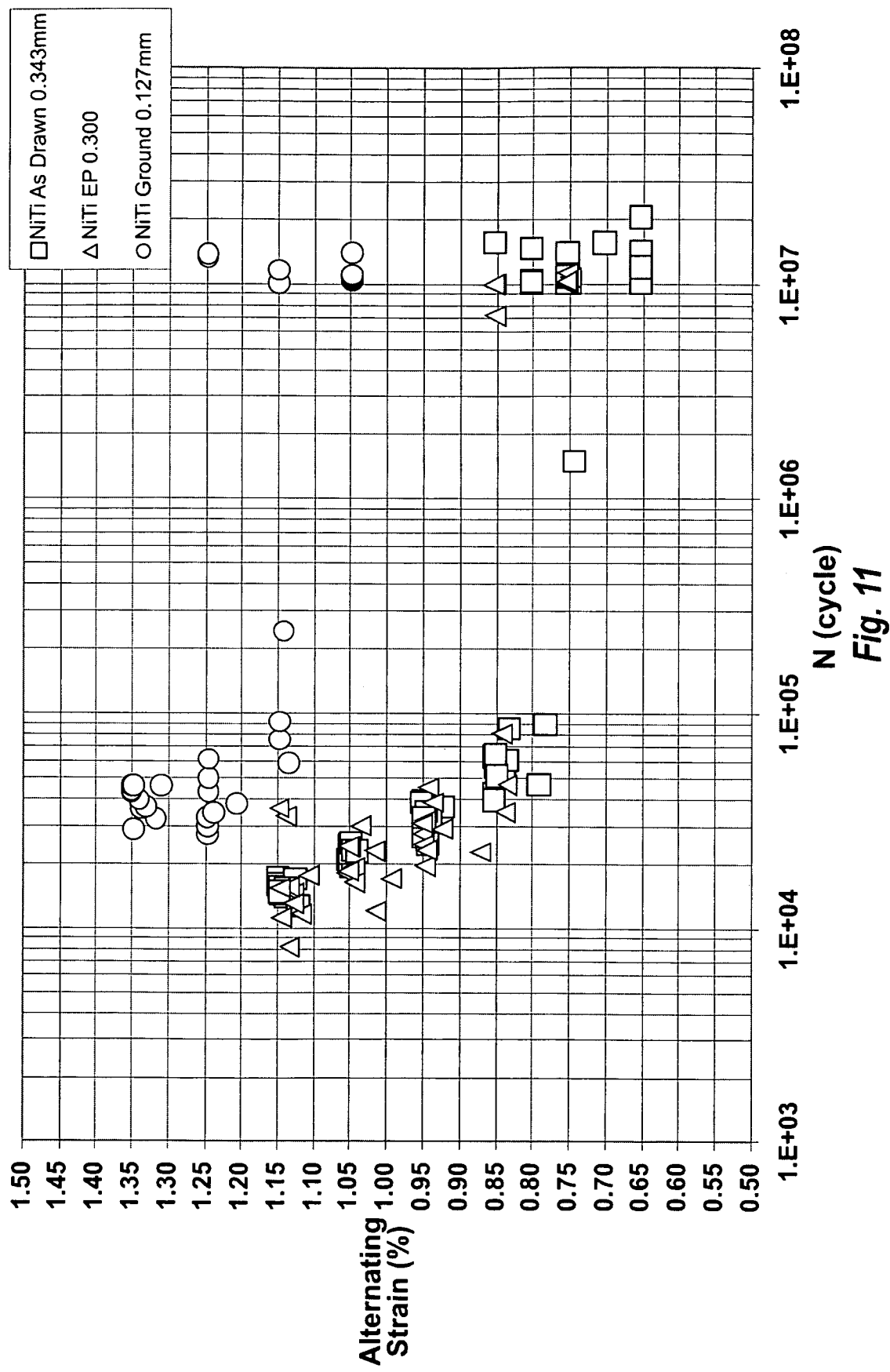
FIG. 11 illustrates a stress-strain plot comparing the fatigue life of samples of nitinol (NiTi) as a function of wire diameter, tested using an apparatus as illustrated in FIG. 1.
Figure 12:
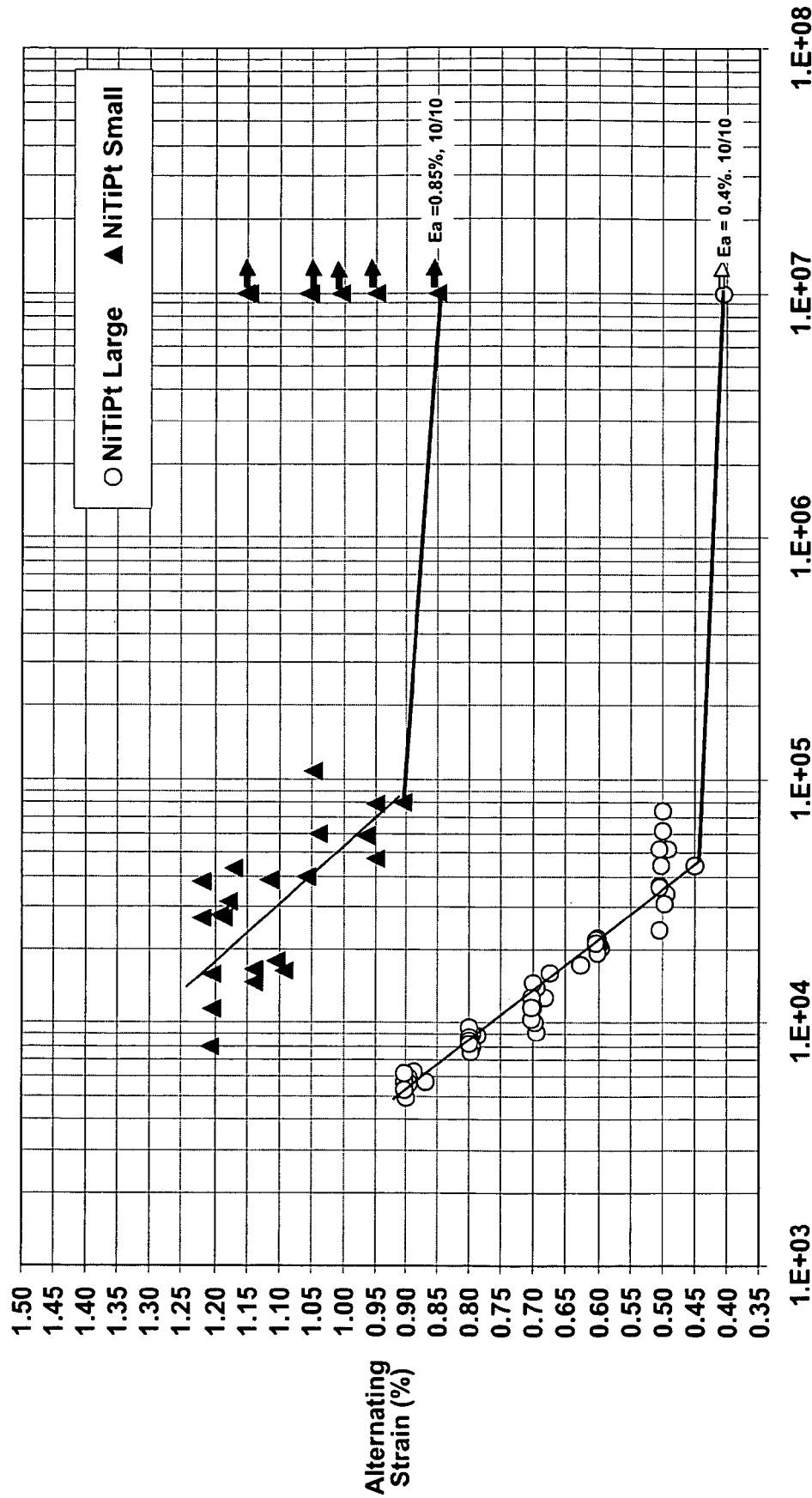
FIG. 12 illustrates a stress-strain plot comparing the fatigue life of samples of a radiopaque nitinol alloy (NiTiPt) as a function of wire diameter, tested using an apparatus as illustrated in FIG. 1.

Data comparing as drawn, electropolished, and ground NiTi wire samples are depicted in FIGS. 10 and 11. For as-drawn specimens, the strain groups were 0.75% and 0.85%; for electropolished specimens, the strain group was 0.85%; for ground, non-electropolished specimens, the strain groups were 1.05% and 1.15%. Data comparing as drawn NiTiPt to ground, non-electropolished NiTiPt are depicted in FIG. 12. Data for NiTiPt are summarized in Table 4.

TABLE 4

| Name | Wire OD | Surface Finish | Strain Limit (%) |
|---|---|---|---|
| NiTiPt Large | 0.343 mm | Drawn/HT | 0.40 |
|  | 0.305 mm | Insuff-EP | 0.65 |
|  | 0.279 mm | EP | 0.75 |
| NiTiPt Small | 0.127 mm | Ground | 0.85 |

Failure analyses on the specimens that failed in the NiTi experiments depicted in FIGS. 10 and 11 are summarized in Table 5 below.

TABLE 5

| Type of Wire | Origin of Failure | Inclusion @ Fracture Origin | Inclusion Size (μm) |
|---|---|---|---|
| As-Drawn (0.343 mm) | Fractures were from TiC inclusions and/or voids. | 10 (11) | 4-6 |
| Electropolished (0.300 mm) | Fractures were from surface defects or TiC inclusions. | 2 (5) | 4-6 |
| Ground (0.127 mm) | Fractures were from surface defects; only one inclusion was found. | 1 (16) | ~2 |

As shown in Table 5, ground wires, had substantially fewer fractures due to inclusions. As a percentage of fractures, about 90% of the fractures in the as-drawn wire were due to inclusions, about 40% of fractures in the electropolished wires were due to inclusions, and only about 6% of fractures in the ground wires were due to inclusions. Surprisingly, the ground wire had a lower percentage of fractures due to inclusions than even the electropolished wires. This result is surprising and unexpected. It has also been found that electropolishing after grinding can result in increased fractures due to inclusions.

Data comparing the fracture probability of as drawn NiTi, electropolished NiTi, and ground NiTi are summarized in Table 6.

TABLE 6

| Alternating Strain (%) | As Drawn Nitinol | | | EP Nitinol | | | Ground Nitinol | | |
|---|---|---|---|---|---|---|---|---|---|
|  | n | r | P (%) | n | r | P (%) | n | r | P (%) |
| 0.71~0.80 | 16 | 2 | 10 | 10 | 0 | 3 | N/A | N/A | N/A |
| 0.81~0.90 | 10 | 9 | 84 | 11 | 5 | 41 | N/A | N/A | N/A |
| 0.91~1.00 | 10 | 10 | 94 | 10 | 10 | 94 | N/A | N/A | N/A |
| 1.01~1.10 | 10 | 10 | 94 | 9 | 9 | 93 | 10 | 0 | 3 |
| 1.11~1.20 | 10 | 10 | 94 | 10 | 10 | 94 | 10 | 10 | 94 |

As seen in Table 6, the probability of fracture for the ground wire at an alternating strain of 1.01%-1.10% was about the same as the probability of fracture of an electropolished wire at an alternating strain of 0.71%-0.80% and substantially lower than the probability of fracture of the as-drawn wire at an alternating strain of 0.71%-0.80%. The forgoing experiments show that memory shape alloys that have been ground to very small diameters can be made fatigue-resistant by grinding rather than solely drawing or electropolishing. Wires made from shape metal alloys can be ground to a thickness of between about 0.04 and 0.45 while still maintaining a suitable fatigue strength for use in medical devices such as stents and/or guide wires.

Example 5

In Example 5, ground nitinol wire is compared before and after fatiguing. It was found that it may be possible to improve the fatigue life of nitinol or R-nitinol by pre-fatiguing or pre-treating the material prior to manufacturing an endoprosthesis therefrom or prior to implanting an endoprosthesis into a patient.

It is believed that pre-fatiguing or pre-treating produces an R-phase material. The R-phase of a superelastic material such as nitinol is a transformation state that the material undergoes when transitioning between an austenitic state and a martensitic state. When a material is within its R-phase, the material may and can have a lower Young's modulus than when in the austenitic phase.

Figure 13:
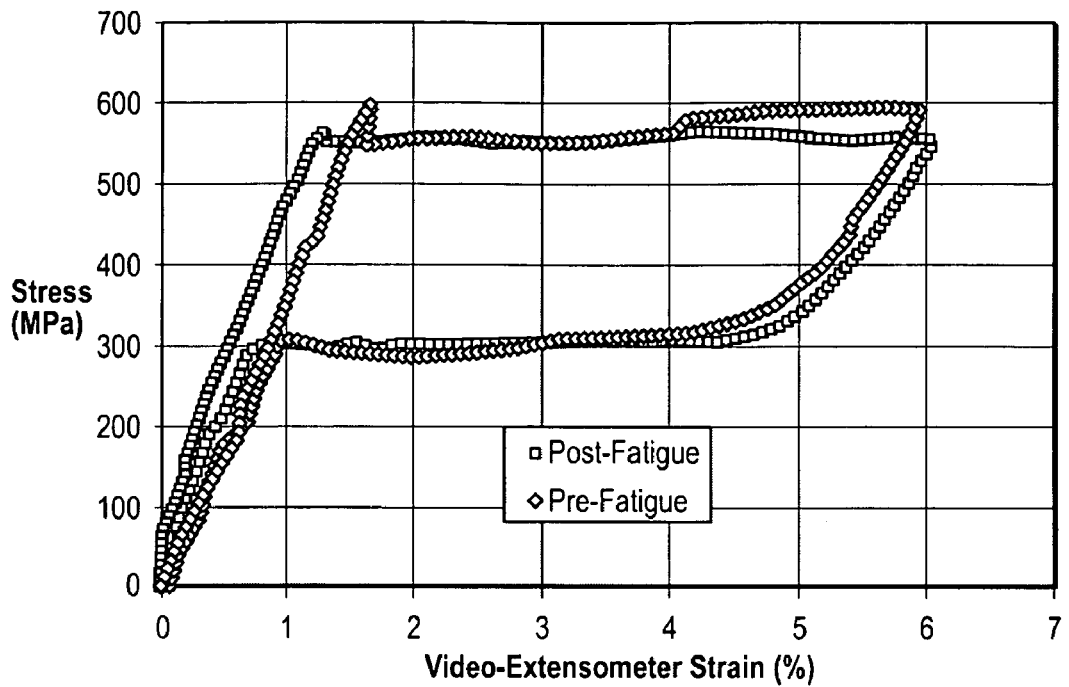
FIG. 13 illustrates stress-strain curves showing the fatigue loading and unloading response nitinol wire before and after fatigue testing.

Ground nitinol wire samples having an outer diameter of approximately 0.13 mm were subjected to stress-strain analysis both before and after fatigue testing using a rotating beam apparatus. The stress-strain curves pre-fatigue and post-fatigue show a Young's modulus shift, which can be seen in FIGS. 13 and 14. FIG. 13 depicts a full stress-stain cycle for pre-fatigue and post-fatigue material. The strain region of stress-strain curves is magnified in FIG. 14, in which the elastic slopes of the lines are compared.

Figure 14:
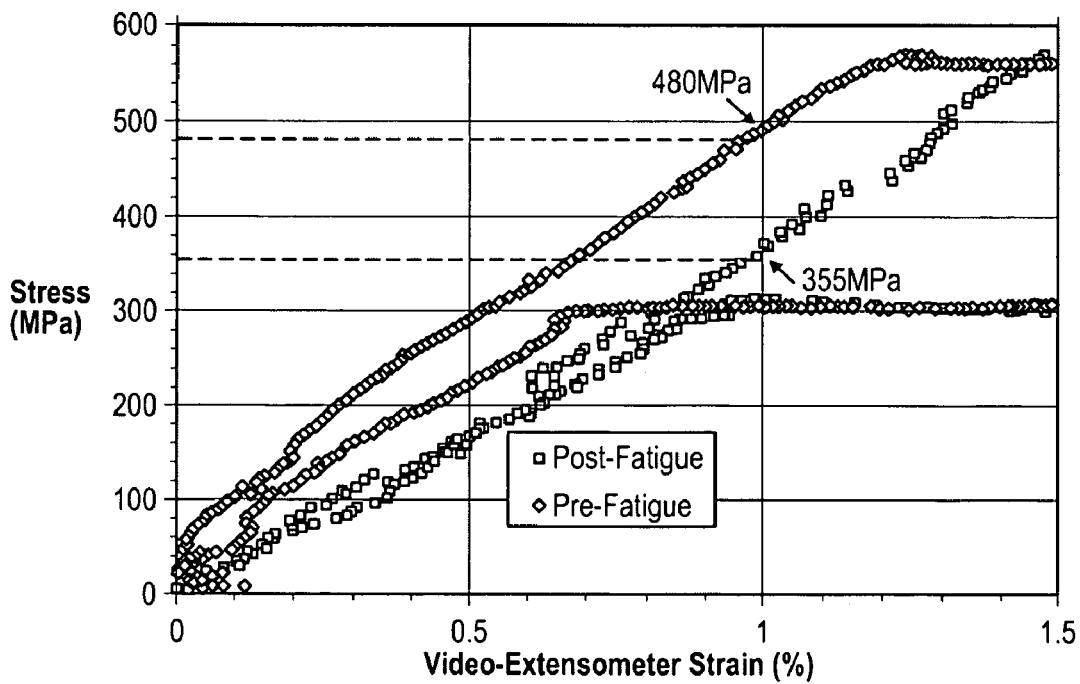
FIG. 14 illustrates a magnified view of the stress region of the stress-strain curves of FIG. 13 showing a shift in the Young's modulus of the nitinol material following fatigue testing.

As can be seen in FIG. 14, for a strain of 1% the tensile stress is reduced in the post-fatigue material from approximately 480 MPa to approximately 355 MPa. It is believed that the reduction in tensile stress give the material a better chance to survive the types of cyclic stress that are typically encountered when an endoprosthesis is implanted in a body. That is, a benefit of a lowering the Young's modulus (as measured by tensile stress) is that for a given strain the stress on the device constructed of the material will be less. Therefore, in designing a medical device such as a stent, it may be desirable to produce a stent of a material within its R-phase, such that the stent would have a greater fatigue life or resistance than one not constructed of a material within its R-phase.

Various embodiments of the methods described herein may be combined with other described embodiments to produce a fatigue resistant medical device. However, the disclosure is susceptible to various modifications and alternative means, and specific examples thereof have been shown by way of example in the drawings and are herein described in detail. It should be understood, however, that the disclosure is not to be limited to the particular devices or methods disclosed, but to the contrary, the disclosure is to cover all modifications, equivalents, and alternatives falling within the spirit and scope of the claims.

We claim:

1. A fatigue-resistant superelastic or shape-memory alloy article, comprising:
    an elongated body including an outer region and an inner core region about which the outer region extends, the elongated body formed at least partially from a superelastic or shape-memory alloy including:
    about 54 atomic % nickel to about 50 atomic % nickel;
    about 46 atomic % titanium to about 50 atomic % titanium; and
    exhibiting a minimum fatigue life defined by survival of at least about 10 million strain cycles at a strain greater than about 0.75%, the minimum fatigue life due, at least in part, to the outer region of the elongated body including an R-phase, and the inner core including an austenite phase but not including the R-phase.

2. A fatigue-resistant superelastic or shape-memory alloy article as recited in claim 1, the nickel being about 51 at % and the amount of titanium being about 49 at %.

3. A fatigue-resistant superelastic or shape-memory alloy article as recited in claim 1, further comprising at least one alloying element selected from the group consisting of iridium, platinum, gold, rhenium, tungsten, palladium, rhodium, tantalum, silver, ruthenium, and hafnium.

4. A fatigue-resistant superelastic or shape-memory alloy article as recited in claim 1, the superelastic or shape-memory alloy having an oxygen concentration being less than about 100 ppm.

5. A fatigue-resistant superelastic or shape-memory alloy article as recited in claim 1, the superelastic or shape-memory alloy having an oxygen concentration being less than about 50 ppm.

6. A fatigue-resistant superelastic or shape-memory alloy article as recited in claim 1, the superelastic or shape-memory alloy having a carbon concentration being less than about 100 ppm.

7. A fatigue-resistant superelastic or shape-memory alloy article as recited in claim 1, the superelastic or shape-memory alloy having a carbon concentration being less than about 50 ppm.

8. A fatigue-resistant superelastic or shape-memory alloy article as recited in claim 1, wherein the R-phase is work hardened.

9. A fatigue-resistant superelastic or shape-memory alloy article as recited in claim 1 wherein the superelastic or shape-memory alloy includes:
    oxide-based inclusions having a size of about 2 μm; and
    carbide-based inclusions having a size of about 2 μm.

10. An implantable device, comprising:
    at least one structural member defining an exterior surface and at least one thickness dimension, the at least one structural member sized and configured for implantation into a living subject, the at least one structural member including an outer region extending inwardly from the exterior surface and an inner core region about which the outer region extends, and
    the at least one structural member formed from a superelastic or shape-memory nickel-titanium alloy exhibiting a minimum fatigue life defined by survival of at least about 10 million strain cycles at a strain greater than about 0.75%,
    the minimum fatigue life due, at least in part, to the outer region of the at least one structural member including an R-phase, and the inner core including an austenite phase but not including the R-phase.

11. An implantable device as recited in claim 10, wherein the strain is at least 0.85%.

12. An implantable device as recited in claim 10, wherein the strain is at least 1.05%.

13. An implantable device as recited in claim 12, the superelastic or shape-memory nickel-titanium alloy further comprising at least one additional alloying element selected from the group consisting of iridium, platinum, gold, rhenium, tungsten, palladium, rhodium, tantalum, silver, ruthenium, and hafnium.

14. An implantable device as recited in claim 10, the at least one thickness dimension in a range from about 0.05 mm to about 0.3 mm.

15. An implantable device as recited in claim 10, the at least one thickness dimension in a range from about 0.1 mm to about 0.25 mm.

16. An implantable device as recited in claim 10, wherein the exterior surface is a ground surface that is substantially free of inclusions.

17. An implantable device as recited in claim 10, wherein the exterior surface is a ground surface that is substantially free of surface defects.

18. An implantable device as recited in claim 10, wherein exterior surface is a ground surface that is a work hardened surface.

19. An implantable device as recited in claim 10, wherein the exterior surface is a ground surface that exhibits an increased toughness relative to at least one non-ground portion of the at least one structural member.

20. An implantable device as recited in claim 10, the superelastic or shape-memory nickel-titanium alloy having an oxygen concentration less than about 100 ppm.

21. An implantable device as recited in claim 10, the superelastic or shape-memory nickel-titanium alloy having a carbon concentration less than about 100 ppm.

22. An implantable device as recited in claim 10, wherein the superelastic or shape-memory alloy includes:
    oxide-based inclusions having a size of about 2 μm; and
    carbide-based inclusions having a size of about 2 μm.

* * * * *